(12) United States Patent
Stähler et al.

(10) Patent No.: US 7,737,088 B1
(45) Date of Patent: *Jun. 15, 2010

(54) METHOD AND DEVICE FOR PRODUCING BIOCHEMICAL REACTION SUPPORTING MATERIALS

(75) Inventors: Cord F. Stähler, Weinheim (DE); Peer F. Stähler, Mannheim (DE); Manfred Müller, München (DE); Fritz Stähler, Weinheim (DE); Hans Lindner, Stuttgart (DE)

(73) Assignee: Febit Holding GmbH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/763,607

(22) PCT Filed: Aug. 27, 1999

(86) PCT No.: PCT/EP99/06316

§ 371 (c)(1),
(2), (4) Date: Apr. 19, 2001

(87) PCT Pub. No.: WO00/13017

PCT Pub. Date: Mar. 9, 2000

(30) Foreign Application Priority Data

| Aug. 28, 1998 | (DE) | 198 39 254 |
| Aug. 28, 1998 | (DE) | 198 39 255 |
| Aug. 28, 1998 | (DE) | 198 39 256 |
| Feb. 19, 1999 | (DE) | 199 07 080 |
| May 27, 1999 | (DE) | 199 24 327 |

(51) Int. Cl.
*C40B 50/14* (2006.01)

(52) U.S. Cl. .................... 506/30; 536/25.31; 536/25.3; 435/6

(58) Field of Classification Search ............... 435/6, 435/283.1, 299.1, 305.1, 970, 973; 536/25.3, 536/25.31; 530/333, 334; 436/518, 527, 436/528, 89

See application file for complete search history.

(56) References Cited

U.S. PATENT DOCUMENTS 4,689,405 A    8/1987   Frank et al.

(Continued)

FOREIGN PATENT DOCUMENTS

CA    2345157 A1   11/1999

(Continued)

OTHER PUBLICATIONS

Davidson, "A microlens direct-write concept for lithography", Institute of Electricla Engineers, vol. 3048, pp. 346-355.

(Continued)

*Primary Examiner*—Christopher Low
*Assistant Examiner*—Christopher M Gross
(74) *Attorney, Agent, or Firm*—Rothwell, Figg, Ernst & Manbeck, P.C.

(57) ABSTRACT

The present invention relates to arrays of biochemical and/or biofunctional elements such as nucleic acids (oligonucleotides, for example) or other biomolecules on a carrier surface and methods of producing such arrays using photoactivation of predetermined areas for synthesis using an illumination matrix that is computer-controlled to generate an exposure pattern. This exposure pattern can be adjusted and monitored by computer using a light sensor matrix, for example a CCD matrix, to allow precise, controlled illumination of specific regions and therefore attachment of array building blocks to those specific regions. The methods and compositions of the invention permit spatially resolved photochemical synthesis of polymer probes on a carrier.

27 Claims, 14 Drawing Sheets

U.S. PATENT DOCUMENTS

| | | | |
|---|---|---|---|
| 5,143,854 A * | 9/1992 | Pirrung et al. | 436/518 |
| 5,239,178 A * | 8/1993 | Derndinger et al. | 250/234 |
| 5,247,180 A | 9/1993 | Mitcham et al. | |
| 5,318,679 A | 6/1994 | Nishioka | |
| 5,384,464 A | 1/1995 | De Fornel et al. | |
| 5,405,783 A | 4/1995 | Pirrung et al. | |
| 5,424,186 A | 6/1995 | Fodor et al. | |
| 5,474,796 A | 12/1995 | Brennan | |
| 5,510,270 A | 4/1996 | Fodor et al. | |
| 5,545,531 A | 8/1996 | Rava et al. | |
| 5,547,839 A | 8/1996 | Dower et al. | |
| 5,624,711 A | 4/1997 | Sundberg et al. | |
| 5,653,939 A | 8/1997 | Hollis et al. | |
| 5,677,195 A | 10/1997 | Winkler et al. | |
| 5,723,320 A | 3/1998 | Dehlinger | |
| 5,728,251 A | 3/1998 | Check, III | |
| 5,736,257 A * | 4/1998 | Conrad et al. | 428/474.4 |
| 5,741,411 A | 4/1998 | Yeung et al. | |
| 5,755,942 A | 5/1998 | Zanzucchi et al. | |
| 5,789,162 A | 8/1998 | Dower et al. | |
| 5,807,525 A | 9/1998 | Allen et al. | |
| 5,812,272 A | 9/1998 | King et al. | |
| 5,843,655 A | 12/1998 | McGall | |
| 5,846,708 A | 12/1998 | Hollis et al. | |
| 5,849,486 A | 12/1998 | Heller et al. | |
| 5,952,172 A | 9/1999 | Meade et al. | |
| 5,968,745 A | 10/1999 | Thorp et al. | |
| 6,001,311 A | 12/1999 | Brennan | |
| 6,020,481 A | 2/2000 | Benson et al. | |
| 6,024,925 A | 2/2000 | Little et al. | |
| 6,066,448 A | 5/2000 | Wohlstadter et al. | |
| 6,114,123 A * | 9/2000 | Murry et al. | 435/6 |
| 6,136,269 A | 10/2000 | Winkler et al. | |
| 6,238,884 B1 | 5/2001 | Short et al. | |
| 6,271,957 B1 * | 8/2001 | Quate et al. | 359/298 |
| 6,295,153 B1 | 9/2001 | Garner | |
| 6,375,903 B1 * | 4/2002 | Cerrina et al. | 422/131 |
| 6,420,169 B1 | 7/2002 | Read et al. | |
| 6,582,917 B1 | 6/2003 | Beier | |
| 6,586,211 B1 | 7/2003 | Stähler et al. | |
| 2002/0160427 A1 | 10/2002 | Beier et al. | |
| 2003/0175781 A1 | 9/2003 | Beier | |
| 2003/0198948 A1 | 10/2003 | Stähler et al. | |
| 2004/0043509 A1 | 3/2004 | Stähler et al. | |
| 2004/0175734 A1 | 9/2004 | Stähler et al. | |
| 2005/0037407 A1 | 2/2005 | Beier et al. | |

FOREIGN PATENT DOCUMENTS

| | | |
|---|---|---|
| CA | 2371938 A1 | 7/2000 |
| DE | 8309254.4 | 1/1985 |
| DE | 04241871 A1 | 6/1994 |
| DE | 69012119 T2 | 12/1994 |
| DE | 04325724 A1 | 2/1995 |
| DE | 69217497 T2 | 6/1997 |
| DE | 69218572 T2 | 11/1997 |
| DE | 19731479 A1 | 8/1998 |
| DE | 69032277 T2 | 12/1998 |
| DE | 69130251 T2 | 5/1999 |
| DE | 19901761 A1 | 7/1999 |
| DE | 19823876 A1 | 12/1999 |
| DE | 19940751 A1 | 3/2000 |
| DE | 19842164 A1 | 4/2000 |
| DE | 19921940 A1 | 6/2000 |
| DE | 19926457 A1 | 7/2000 |
| DE | 69328693 T2 | 8/2000 |
| DE | 19910392 A1 | 9/2000 |
| EP | 0022242 A2 | 1/1981 |
| EP | 0130166 A1 | 1/1985 |
| EP | 0316018 A2 | 5/1989 |
| EP | 0385410 A2 | 9/1990 |
| EP | 0430248 A2 | 6/1991 |
| EP | 0493137 A1 | 7/1992 |
| EP | 0549993 A1 | 7/1993 |
| EP | 0671626 A1 | 9/1995 |
| EP | 0955085 A2 | 11/1999 |
| JP | 9288080 | 11/1997 |
| WO | 98 08085 | 2/1988 |
| WO | WO 90 00626 | 1/1990 |
| WO | WO 91/18276 A1 | 11/1991 |
| WO | WO 92/10092 A1 | 6/1992 |
| WO | WO 93/20230 A1 | 10/1993 |
| WO | WO 93/22678 A2 | 11/1993 |
| WO | WO 94 12632 | 6/1994 |
| WO | WO 94 18226 A1 | 8/1994 |
| WO | WO 95/01559 A2 | 1/1995 |
| WO | WO 95/09176 A1 | 4/1995 |
| WO | WO 95/12808 A1 | 5/1995 |
| WO | WO 95 17413 | 6/1995 |
| WO | WO 96/10747 A1 | 4/1996 |
| WO | WO 96/33971 A1 | 10/1996 |
| WO | WO 96/40712 A1 | 12/1996 |
| WO | WO 97/06468 A2 | 2/1997 |
| WO | WO 97/12030 A1 | 4/1997 |
| WO | WO 97/19749 A1 | 6/1997 |
| WO | WO 97/39151 A1 | 10/1997 |
| WO | WO 97/41425 A1 | 11/1997 |
| WO | WO 97 42330 | 11/1997 |
| WO | WO 98/03683 A1 | 1/1998 |
| WO | 98 13683 | 4/1998 |
| WO | WO 98/30893 A1 | 7/1998 |
| WO | WO 98/51819 A1 | 11/1998 |
| WO | WO 98/53093 A1 | 11/1998 |
| WO | WO 98/58293 A2 | 12/1998 |
| WO | WO 99/09042 A2 | 2/1999 |
| WO | WO 99 14318 | 3/1999 |
| WO | WO 99/19510 A1 | 4/1999 |
| WO | WO 99 25724 A2 | 5/1999 |
| WO | WO 99/27140 A1 | 6/1999 |
| WO | WO 99/31275 A1 | 6/1999 |
| WO | WO 99/37819 A2 | 7/1999 |
| WO | 99 41007 | 8/1999 |
| WO | 99 42813 | 8/1999 |
| WO | WO 99/39817 A1 | 8/1999 |
| WO | 99 60156 | 11/1999 |
| WO | WO 99/60170 A1 | 11/1999 |
| WO | 99 63385 | 12/1999 |
| WO | WO 00/11473 A1 | 3/2000 |
| WO | WO 00 13017 | 3/2000 |
| WO | WO 00/13017 A2 | 3/2000 |
| WO | WO 00/13018 A3 | 3/2000 |
| WO | WO 00 49142 A1 | 8/2000 |
| WO | WO 00 53617 A1 | 9/2000 |
| WO | WO 02/32567 A1 | 4/2002 |

OTHER PUBLICATIONS

Bertsch et al., "Study of the spatial resolution of a new 3D microfabricationprocess . . . " Chemical Abstracts, vol. 127, No. 15, Oct. 13, 1997.

Sangeet et al., "Maskless fabrication of light-directed oligonucleotide microarrays using a digital micromirror array", Nature Biotechnology, vol. 17, Oct. 1999, pp. 974-978.

Retrieved form the Internet: "Digital Opitical Chemistry", retrieved on Dec. 20, 1999.

Johnson et al., "Micromirror arrays perform photolithography step", EETIMES. COM Online, Dec. 20, 1999.

Bertsch et al., "Study of the spatial resolution of a new 3D microfabrication process . . . ", Chemical Abstracts, vol. 127, No. 15, Oct. 13, 1997.

U.S. Appl. No. 60/087,333, filed May 29, 1998, Quate et al.

Bertsch et al., "Study of the Spatial Resolution of a New 3D Microfabrication Process: The Microstereophotolithography Using a Dynamic Mask-generator Technique," J. Photochemistry Photobiology A: Chemistry 107:275-281, 1997.

Hanley, et al. "Charge Transfer Device in Analytical Instrumentation," Anal. Chem. 68:A661-A667, 1996.

Hoheisel, "Oligomer-Chip Technology," Trends Biotechnol. 15(11):465-469, 1997.

Kirschner, et al., "Miniaturisierte NIR-Diodenarray-Spektrometer," GIT Labor-Fachzeitschrift (English Title Translation: Miniaturizated NIR Diode Array Spectrometers), 402-404, 1998.

Neff, et al., "Two-Dimensional Spatial Light Modulators: A Tutorial," Proc. IEEE, 78(5):826-854, 1990.

Villemoes et al., "A Computerized Peptide Synthesizer with Feed back Control," Acta Chemica Scand. B 32:703-713, 1978.

von Buren et al., "Branched Oligodeoxynucleotides: Automated Synthesis and Triple Helical Hybridization Studies," Tetrahedron Lett. 51(31):8491-8506, 1995.

Beattie and Fowler, "Solid-phase gene assembly", *Nature*, 352:548-549, 1991.

Khudyakov et al., "Synthetic Gene for the Hepatitis C Virsu Nucleocapsid Protein," Nucl. Acids Res. 21(11):2747-2754, 1993.

Lashkari et al., "An Automated Multiplex Oligonucleotide Synthesizer: Development of High-Throughput, Low-Cost DNA Synthesis" Proc. Natl. Acad. Sci. USA 92(17):7912-7915, 1995.

Mullis et al., "Specific Enzymatic Amplification of DNA in Vitro: The Polymerase Chain Reaction," Cold Spring Harbor Symposia on Quantitative Biology, vol. LI, pp. 263-273, Copyright 1986 Cold Spring Harbor Laboratory.

Rayner, S. et al., "MerMade: An oligodeoxyribonucleotide synthesizer for high throughput oligonucleotide production in dual 96-well plates" *PCR Methods and Applications*, US, Cold Spring Harbor, NY, 8(7):741-747, 1998.

Sindelar, L.E. et al., "High-throughput DNA synthesis in a multichannel format" *Nucleic Acids Research* 23(6):982-987, 1995.

Stemmer, W.P.C., et al., "Single-step assembly of a gene and entire plasmid from large numbers of oligodeoxynucleotides" Gene 164:49-53, 1995.

Weiler, J. et al., "Combing the Preparation of Oligonucleotide Arrays and Synthesis of High-Quality Primers" Anal. Biochem. 243:218-227, 1996.

Search Report from the German Patent and Trademark Office issued Aug. 9, 1999 and English Translation Thereof.

Search Report from the German Patent and Trademark Office issued Apr. 17, 2000 and English Translation Thereof.

\* cited by examiner

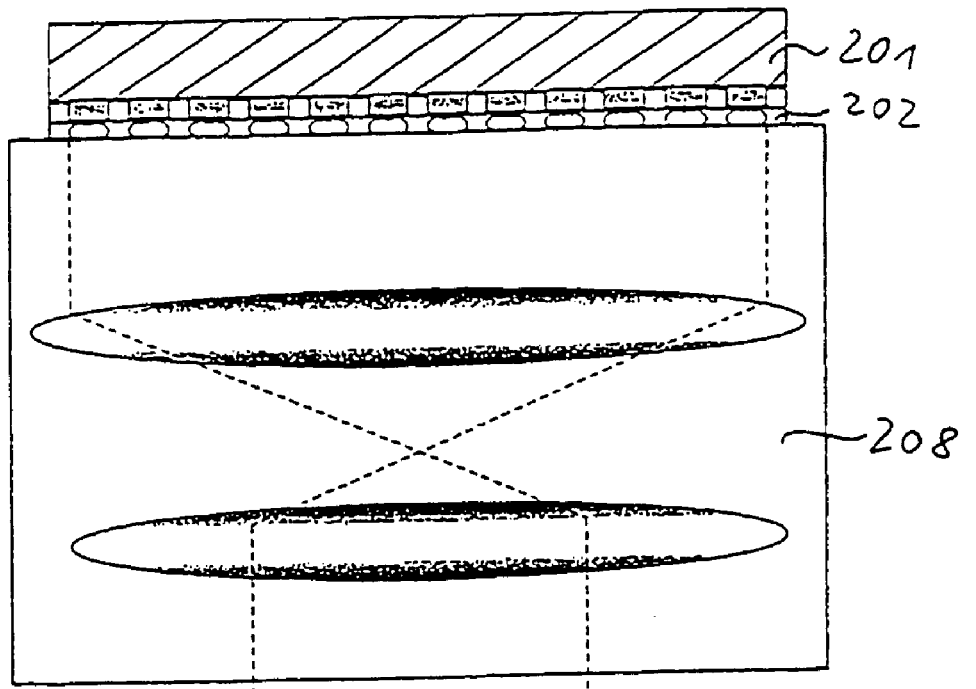
Fig. 10
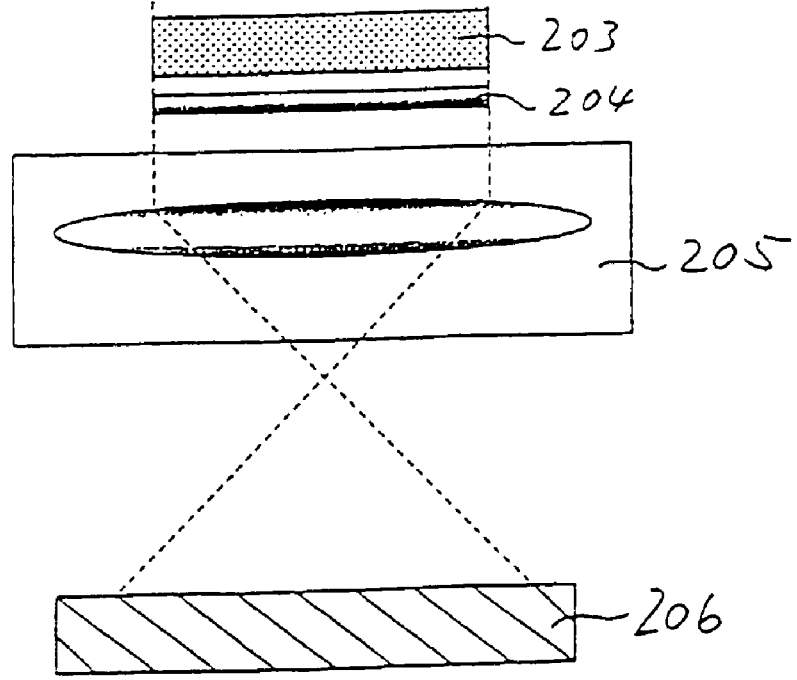

METHOD AND DEVICE FOR PRODUCING BIOCHEMICAL REACTION SUPPORTING MATERIALS

The invention relates to the use of an illumination matrix which can be controlled to generate an optionally adjustable exposure pattern, in particular a programmable light source matrix, in the field of biotechnology in general and for preparing, manipulating and analyzing opto-fluidic reaction carriers in particular.

Miniaturizing and at the same time functionally integrating elements, components and whole systems make novel applications available in many technologies. Said applications extend from sensor technology via microsystem technology (e.g. complex biochips using semiconductor technology) to actuator technology (e.g. in the form of micropumps). The industries extend from classical mechanical engineering via automotive and aviation industries to medical technology and the forward-looking biotechnology. In medical technology, for example, new implants are developed and the pharmaceutical industry advances new technologies for efficient development of novel medicaments and diagnostic systems at enormous cost. Owing to its great potential, biotechnology in particular profits from said development.

Novel methods which make use of the changed peripheral conditions are developed for economical production in the field of microtechnology. The same is true for the inspection techniques required for monitoring the miniaturized processes.

For basic research in the life sciences and for medical diagnostics and some other disciplines, gathering biologically relevant information (mostly in the form of genetic information) in defined examination material is extraordinarily important. In this context, the genetic information is present in the form of an enormous variety of different nucleic acid sequences, the DNA (deoxyribonucleic acid). Realization of said information leads, via producing transcripts of DNA into RNA (ribonucleic acid), mostly to the synthesis of proteins which for their part are commonly involved in biochemical reactions.

A powerful system format for gathering said wealth of information is the so-called biochip. Biochips in this connection mean highly miniaturized, highly parallel assays. Detecting particular nucleic acids and determining the sequence of the four bases in the nucleotide chain (sequencing) produces valuable data for research and applied medicine. In medicine, it was possible, to a greatly increasing extent through in-vitro diagnostics (IVD), to develop and provide to the doctor in charge equipment for determining important patient parameters. For many diseases, diagnosis at a sufficiently early stage would be impossible without said equipment. Here, genetic analysis has been established as an important new method (e.g. case diagnosis of infectious diseases such as HIV or HBV, genetic predisposition for particular cancers or other diseases, or in forensic science). Close interaction between basic research and clinical research made it possible to elucidate the molecular causes and (pathological) connections of some diseases down to the level of genetic information. This development, however, has only just started, and greatly intensified efforts are necessary, particularly for the conversion into therapy strategies. Overall, the genome sciences and nucleic acid analysis connected therewith have made important contributions both to the understanding of the molecular bases of life and to the elucidation of very complex diseases and pathological processes. Moreover, genetic analysis or analysis through genetic engineering already now provides a broad spectrum of diagnostic methods.

Further development in medical care is hampered by the explosion in costs related to correspondingly expensive methods. Thus, determining genetic risk factors by sequencing at the moment still costs several hundred to several thousand US dollars. It is necessary here not only to demand implementation of possible diagnostic and therapeutic benefits, but also to advance integration into a workable and affordable healthcare system.

Likewise, applying appropriate technologies in research can take place on a large scale and also at universities only if the costs related thereto are reduced. Here, a change in paradigms of research in life sciences begins to emerge:

The bottleneck of deciphering primary genetic information (sequence of bases in the genome) and detecting the state of genetic activity (genes transcribed into messenger RNA) of cells and tissues is removed by the availability of sufficiently cheap, powerful and flexible systems. It is then possible to concentrate, work on the (very complex) task of analyzing and combining the relevant data. This should result in new levels of knowledge for biology and subsequently in novel biomedical therapies and diagnostic possibilities.

The biochips already mentioned before are miniaturized hybrid functional elements with biological and technical components, for example biomolecules which are immobilized on the surface (outer surface or/and inner surface) of a carrier and which may serve as specific interaction partners, and a matrix, for example silicon matrix. Frequently, the structure of said functional elements has rows and columns; this is known as a chip array. Since thousands of biological or biochemical functional elements may be arranged on such a chip, microtechnical methods are usually needed to prepare said elements.

Essentially, two principles are used as methods for preparing said arrays: application of finished probes or functional elements to the reaction carrier, which is the predominantly used method at the moment, or in-situ synthesis of the probes on the carrier. The devices used for both principles are so-called microfluidic spotters. In-situ synthesis may also use photolithographic methods.

Possible biological and biochemical functional elements are in particular: DNA, RNA, PNA, (in nucleic acids and chemical derivatives thereof, for example, single strands, triplex structures or combinations thereof may be present), saccharides, peptides, proteins (e.g. antibodies, antigens, receptors), derivatives of combinatorial chemistry (e.g. organic molecules), cell components (e.g. organelles), cells, multicellular organisms, and cell aggregates.

A multiplicity of photolithographic systems for exposure-dependent generation of fine and very fine structures using light of different wavelength (energy) of down to below 200 nm are commercially available for applications in semiconductor technology. The finer the structures to be generated, the shorter the wavelength used has to be. Thus, structures in the sub-µm range which are already in the range of visible-light wavelengths (400-800 nm) can only be generated using high energy radiation of distinctly shorter wavelength. Photolithographic systems consist in principle of a lamp as energy or light source and a photolithographic mask which has transparent and nontransparent areas and thus generates an exposure pattern in the transmitted-light course of ray. Optical elements reproduce said exposure pattern on the object to be exposed (e.g. reduced by a factor of 100). A line on the mask is thereby reduced in width from 0.1 mm to 10 µm. Preparing a microstructure in or on a silicon wafer commonly requires 10 to 30 exposure steps. The systems are geared to said number and facilitate automatic mask switching by means of magazines and operating tools.

Thus, an almost macroscopic structure of the mask results in a microstructured image on the object to be exposed, for example the silicon wafer. To generate a photolithographic mask, photolithographic systems are likewise employed again which, of course, need only a correspondingly lower resolution and also, depending on the preparation method, only a correspondingly smaller energy input. This is a cyclic process which has been very far advanced and perfected due to the large market volume of the semiconductor industry.

GeSim already uses for the production of photolithographic masks LCD photo plotters from Mivatec. This is possible, since the mask structures, with respect to structure size and required wavelength, allow exposure in the visible-light range. This makes a relatively fast and relatively flexible production of masks possible. This is sufficient in semiconductor technology owing to the limited number of masks required, since only a functional test shows the success of the microstructuring and thus there is usually always enough time for producing new or improved masks. Overall however, producing the masks is expensive, time-consuming and not very flexible.

Using photolithography for the light-induced in-situ synthesis of DNA (synthesis directly on the biochip), Affymax Institute and Affymetrix already use commercial exposure systems for preparing high-density DNA microarrays (references: U.S. Pat. No. 5,744,305, U.S. Pat. No. 5,527,681, U.S. Pat. No. 5,143,854, U.S. Pat. No. 5,593,839, U.S. Pat. No. 5,405,783). The wavelength employed is restricted to 300-400 nm. Each change in the exposure pattern requires a mask change. This is extremely restricting since preparing, for example, a DNA array with oligonucleotides of 25 building blocks in length (25-mers) per slot requires approx. 100 individual exposure cycles.

In general, the reaction carriers have a 2D base area for the coating with biologically or biochemically functional materials. The base areas may also be formed, for example, by walls of one or more capillaries or by channels. An extension of the geometry is a 3D structure in which analyzing and, where appropriate, also manipulating or controlling the reactions take place in a 2D arrangement.

Especially in the USA, enormous resources are used to advance the development of miniaturized biochips.

Regarding the prior art, the following publications are referred to, for example:
1. Nature Genetics, Vol. 21, supplement (complete), January 1999 (BioChips)
2. Nature Biotechnology, Vol. 16, pp. 981-983, Oct. 1998 (BioChips)
3. Trends in Biotechnology, Vol. 16, pp. 301-306, July 1988 (BioChips).

Important application fields for miniaturized, parallel assays and thus for applying the present invention are:

molecular diagnostics (including in-vitro diagnostics, clinical diagnostics, genetic diagnostics)/development of pharmaceuticals (substance development, testing, screening etc.)/biological basic research (i.a. genomics, transcriptomics, proteomics, physiomics)/-molecular interactions/analysis and screening of pathogens (viroids, prions, viruses, prokaryotes, eukaryotes)/oncology/environmental monitoring/food analysis/forensic science/screening of medical products (i.a. blood products)/detection, analysis and screening of transgenics (plants, animals, bacteria, viruses, breeding, outdoor trials)/cytology (i.a. cell assays)/histology/all types of nucleic acid analyses (i.a. sequence analysis, mapping, expression profiles)/SNPs/pharmacogenomics/functional genomics.

The object of the invention is to provide a method and a device which facilitate relatively flexible and relatively fast preparation and relatively efficient analysis of miniaturized highly parallel reaction carriers.

BRIEF DESCRIPTION OF THE DRAWINGS

FIG. 10 shows an embodiment as for FIG. 9, but where the reduction is achieved using a suitable lens system.

Figure 1:
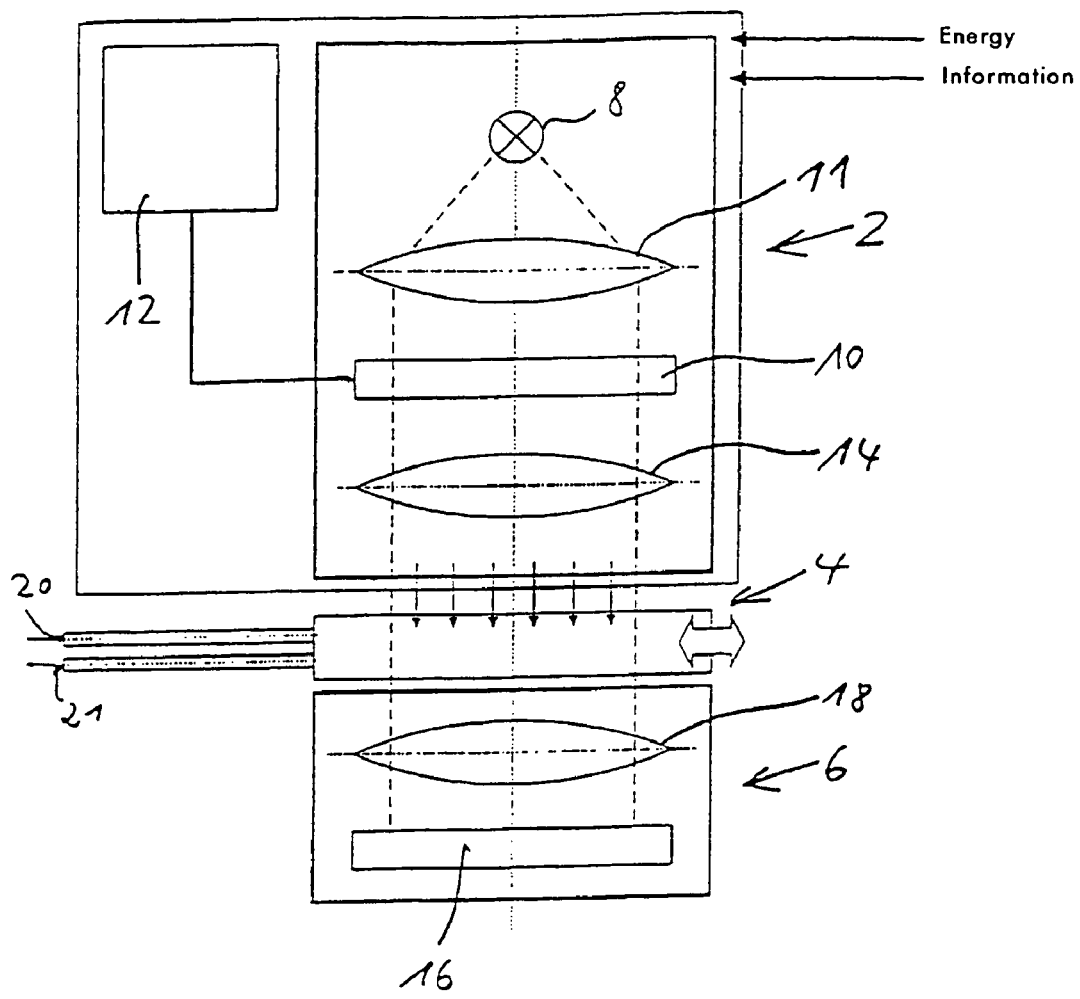
FIG. 1 depicts an arrangement for preparing a biochip or/and for manipulating or/and for studying biologically or biochemically functional materials immobilized thereon.

Method and device should in addition facilitate integration of preparation and analysis into one apparatus. Furthermore, it is intended to create a basis for completely automating all processes in preparation and analysis.

The method of the invention for preparing a reaction carrier coated with biologically or biochemically functional materials comprises the following steps:
(a) providing a carrier having a surface which has photoactivatable groups,
(b) activating the photoactivatable groups on at least one predetermined area of the carrier surface by location-specific exposure of the carrier using an illumination matrix which can be controlled to generate an optionally adjustable exposure pattern,
(c) location-specific binding of biologically or chemically functional materials or building blocks for such materials on at least one of the predetermined areas and
(d) where appropriate, repeating the activation and binding steps on the same or/and different predetermined areas.

The carrier is a solid phase which can be or is equipped with biochemical or biological materials or receptors or building blocks thereof. The carrier may have a planar surface or a surface provided with grooves, for example channels. The channels are preferably microchannels of, for example, from 10-1000 µm in cross section. The channels may be—depending on the surface properties—capillary channels but also channels without capillary action (e.g. owing to Teflon coating). The carrier is at least partially optically transparent in the area of the reaction areas to be equipped.

The use of an illumination matrix which can be controlled to generate an optionally adjustable exposure pattern, facilitates great flexibility in the preparation or/and manipulation or/and analysis of opto-fluidic reaction carriers and, in particular, faster preparation of reaction carriers than previously possible. In contrast to generating correspondingly fine-resolution exposure patterns in a photolithography machine by means of invariant individual masks which have to be changed when changing the exposure pattern, using a controllable illumination matrix can in principle generate and alter any possible exposure pattern by simply controlling the illumination matrix from a control computer. Thus, in one production process it is in principle possible to generate and analyze in one day hundreds to thousands of different reaction carriers having a multiplicity of individual reaction areas, something which has been impossible up until now.

The predetermined reaction areas for which a location-specific exposure of the carrier is to be carried out are selected for an actual application preferably automatically by a program which facilitates controlling and assigning the reaction areas to one or more reaction carriers according to the criteria synthesis efficiency, optimal synthesis conditions, for example temperature etc., optimal analysis conditions, for example hybridization temperature with respect to neighboring areas. After preparing the carrier, it may be provided for, where appropriate, to change the carrier and to continue the process from step (a) onward. In this context, step (c) may include the location-specific binding of biologically or chemically functional materials or building blocks for such materials in the same way as in the preceding cycle or else taking into account the information from a preceding synthesis cycle.

Programmability and electronic controllability of the illumination matrix remove the exchange and also generation of the mask units as were required for the photolithographic methods. Generating the exposure patterns thus is no longer connected with expenses for preparing, exchanging, positioning, storing and optimizing exposure masks. This makes in particular the in-situ synthesis of reaction carriers (e.g. DNA microarrays) accessible to wide use. According to a preferred embodiment of the invention, an illumination matrix is used which is able to illuminate with a resolution of at least 500 points per cm$^2$.

The illumination matrix and the assigned light source serve in principle to provide the desired exposure pattern for controlling/exciting photochemical processes or, where appropriate, for analyzing a reaction carrier matrix. According to a variation, it is possible to optionally modulate the light intensity and/or wavelength of each luminous spot of the illumination matrix or of the exposure pattern on the reaction carrier.

The illumination matrix used is preferably a controllable reflection matrix which reflects light location-selectively, according to its control, in a particular direction (here in the direction of the reaction carrier). Such reflecting surface light modulators having controlled deformable mirror arrangements for generating light patterns can be in particular light modulators having viscoelastic control layers or light modulators having micromechanical mirror arrays. Regarding the technology of such light modulators having viscoelastic control layers and light modulators having micromechanical mirror arrays, relevant data sheets of the Fraunhofer Institute for Microelectronic Circuits and Systems are referred to and are attached to this application. The advantage of such controllable reflection matrices is in particular that they are available for a wide spectral range from UV to IR light, for example in a wavelength range from 200-2000 nm. The newest developments of controllable reflection matrices in 40V-CMOS technology are advantageous in particular for transmitting high-energy radiation in the UV range and also in general at high energy densities per area. Due to the working voltage of 40 V, the matrices are correspondingly insensitive. A further advantage is that a reflection matrix of this type facilitates an exposure parallel in time of all sites to be exposed in the exposure pattern at appropriate illumination using a light field extending across the matrix area. This possibility of parallel exposure of a reaction carrier has consequences for the length of the preparation (for in-situ syntheses), for the possibilities of online control and evaluation (no artefacts due to time gaps between points of measurement etc.) and for possible manipulations, for example in the case of cell arrays or other biological components of a reaction carrier (for example in the case of retina preparations or light-dependent neuronal activity).

As long as parallel exposure is not crucial, it is possible, instead of uniform illumination of the illumination matrix to carry out screening or scanning of the illumination matrix using a bundled beam, for example a laser beam, in order to generate the desired light pattern on or in the reaction carrier, according to the control of the illumination matrix. It is thus possible to utilize a wide variety of light sources, for example also light sources whose emission spectrum or emission wavelength can be optionally altered, e.g. an $N_2$ laser, so that, for example, a plurality of signal-generating fluorescent substances on or in the reaction carrier can be excited using different wavelengths (this is a kind of 2D spectroscopy).

Another class of possible illumination matrices for the use according to the present invention is represented by light source arrays, i.e. matrix-like arrangements of very small light sources which can be controlled individually. These can be, for example, microlaser arrays, microdiode arrays or the like. UV-light emitting diodes are available now whose emission wavelength is 370 nm. Such UV-light emitting diodes are sold under the type designations NSHU 590 and NSHU 550 by Roithner Lasertechnik, A-1040 Vienna, Fleischmanngasse 9. The corresponding UV-light emitting diode technology can be used for preparing a diode array, in particular microdiode array.

Therefore, the individually controllable spots of such a light source array (light source matrix) correspond to the individual illumination spots on the reaction carrier in the individual reaction areas, it being possible for the generated exposure pattern to be reduced in size, if necessary, with the aid of suitable optical components.

Such a (self-luminous) light source matrix is different from illumination matrices working as "light valves" such as, for example, LCDs and those working as light reflectors such as, for example, controllable micro-mirrors. A technical solution for a light source array can be structures based on gallium nitride (GaN) in a two-dimensional arrangement. GaN is known as a UV emitter, for example from the preparation of commercially available UV LEDs. A matrix having many independently controllable elements is built from said structures through suitable wiring. Furthermore, a correspondingly built microlaser array is conceivable in which, for example, GaN can be used as laser-active medium.

Such a device may consist of, for example, a matrix of emitting semiconductor elements emitting light of wavelength <400 nm, as is done for example by GaN light emitting diodes. As mentioned, a possible illumination matrix is also a correspondingly built microlaser array. The size of a light emitting element may be in a range between 500×500 µm and 50×50 µm. Each matrix element can be separately controlled. For an exposure as the starting point of a biochemical reaction, at least one light emitting diode emits photons within a wavelength range below 400 nm. Since the device has been designed preferably as a unit for initiating spatially separated photochemical reactions in a reaction carrier, the illumination matrix needs to be less than 75% occupied with light emitting elements. The size of the light source matrix is larger than or equal to the optical image on the reaction carrier. Minimizing the image may be required and is preferably achieved by lightwave conduction in a glass fiber bundle (fused fiber optic taper), optionally also by suitable lens systems. Fused fiber optic tapers are known to be employed in nightvision devices, for example.

The arrangement pattern of the UV-light emitting diodes preferably corresponds to the pattern of the synthesis positions in the reaction carrier.

The structure of the illumination component (self-luminous light source matrix) thus consists of a matrix on which UV-light emitting diodes or microdiode lasers are arranged in rows and columns. The individual light source elements of said matrix are controlled to generate a specific exposure pattern which corresponds to the pattern of the synthesis positions in the reaction carrier.

The individual light source elements are controlled, for example, row- and columnwise which causes pulsating of the individual light emitting diodes or laser elements, i.e. a variable light intensity is emitted. A similar method of control can be found, for example, in LCD illumination matrices. Alternatively, the individual light emitting diodes of the matrix can be statically controlled by flip-flops or DRAMs and also by other suitable switches.

The light source array may be immediately followed by a matrix made from optical microelements (or else a mechanical shadow mask to suppress light scattering). This component may consist for its part of one of several interconnected layers of microscopic optical elements (e.g. microlenses) and is expediently mounted directly on the light source matrix.

In one embodiment, the microoptical component is immediately followed by a fused fiber optic taper which serves to minimize the illumination pattern in a 1:1, 2:1, . . . 25:1 ratio (entrance:exit) or possible intermediate values. Here, the individual fibers of the fused fiber optic taper may be isolated from one another by a black sheathing.

Between the individual components of the device there may be a fluidic optical medium. The exposure pattern generated may for its part be coupled into the reaction carrier via a fused fiber optic taper which is mounted directly on the surface of the planar reaction carrier.

The possible structure of the reaction carrier and the arrangement of a light sensor matrix (multichannel detector matrix) which is preferably provided in the form of a CCD chip is explained in the following.

The reaction carrier is arranged on the light-emitting side of the light source matrix. The reaction carrier is optically transparent at least on the side facing the illumination matrix. This makes it possible to generate a spatially resolved exposure pattern in this reaction carrier, which can be an optofluidic microprocessor, for example. In this way, it is possible to control in a spatially resolved manner immobilizing or synthesizing polymer probes in the reaction carrier by using suitable photochemistry within the individual reaction areas.

A device for implementing the method described can be built in a very compact and space-saving way and may then carry out both synthesis activation on the reaction carrier and thus doping the reaction areas with the appropriate polymer probes, and signal detection after adding sample material.

Between the reaction carrier and the relevant light sensor matrix a spectral filter (bandpass or longpass) may be present which facilitates spectral separation of the signal light from the exciting light in the fluorimetric detection of the analytes bound to the biochip (reaction carrier). Moreover, using a filter wheel containing various optical filters allows simultaneous detection of analytes of various sample materials which have been labeled by different fluorophores with fluorescence maxima far apart in the spectrum.

The operating modes of the light source matrix (illumination matrix) and the relevant light sensor matrix (e.g. CCD array) can be synchronized by either suitable hardware or software. If the individual elements of the illumination matrix can be switched on a nanosecond timescale without, for example, "afterglow", then electronic synchronisation with a so-called gated CCD camera via an external frequency generator is also possible. Since the fluorescence lifetime of common fluorophores is usually a few nanoseconds long, in this way separation in time of the exciting light and the signal light is possible for the fluorimetric detection of the analyte so that time-resolved spectroscopy can be carried out.

Another class of illumination matrices which can be used according to the invention is represented by matrix arrangements of "light valves" or controllable transmitted-light modulators which can be controlled location-selectively in order to let or not to let light through. Said devices are electronic components in which the light of a light source falls on a matrix of controllable pixels. Each pixel can be modulated by the electronic control signal with respect to its optical transparency. Thus a controllable light valve matrix LVM is created. In order to fulfill the function of the light valve, parts of the electronic components (i.a. the actual electrodes) have to be transparent. The group of light valves includes as its most prominent representative the liquid crystal display LCD. Light valves based on LCD are very common, as micro version i.a. in the viewfinder of digital videocameras and in nightvision devices, and as macro version, for example, in laptops or as display for personal computers. Transmission in the dark state is still up to 10% of the amount of light coming in from the back, though. LCDs are available for transmitted light wavelengths of above 400 nm. For exposure in the UV range, the contained crystals are badly suited, i.a. owing to their intrinsic absorption (see i.a. Microsystem Technologies 1997, 42-47, Springer Verlag). For configuring LVMs in the UV range, therefore, other substances are necessary as filling between the transparent electrodes. Such alternative substances are known, for example, from so-called suspended particle devices SPD (see i.a. U.S. Pat. No. 5,728,251). These and other substances can be used with the same electrode arrangement as LCDs, but it is also possible to use other transparent components.

The method of the invention may provide for the carrier to be exposed to pulsating, coherent, monochromatic, parallel radiation or/and, where appropriate, to radiation which can be focused in different planes.

The reaction carrier or biochip may have, for example, a semiconductor surface, a glass surface or a plastic surface for coating with biologically or biochemically functional materials, which surface may be an outer surface or/and an inner surface of the carrier, the latter, as long as the carrier is at least partially hollowed out, for example has channels running through. Preference is given to using a transparent carrier which facilitates optical studies in transmitted light mode.

The predetermined activatable areas may include, for example, an area of from 1 µm$^2$ to 1 cm$^2$, in particular 100 µm$^2$ to 1 mm$^2$. The predetermined activatable areas may be surrounded by nonactivated or/and nonactivatable areas.

The illumination matrix may have a pattern inherent to the predetermined activatable areas, for example with sites which cause always shading or darkness in the exposure pattern.

The biologically or biochemically functional materials are selected preferably from biological substances or from materials reacting with biological substances, namely preferably from nucleic acids and nucleic acid building blocks, in particular nucleotides and oligonucleotides, nucleic acid analogs such as PNA and building blocks thereof, peptides and proteins and building blocks thereof, in particular amino acids, saccharides, cells, subcellular preparations such as cell organelles or membrane preparations, viral particles, cell aggregates, allergens, pathogens, pharmacological active substances and diagnostic reagents.

The biologically or biochemically functional materials are preferably synthesized on the carrier in two or more stages from monomeric or/and oligomeric building blocks.

The great flexibility of the method according to the invention facilitates generating an expansive substance library having a multiplicity of different biologically or chemically functional materials on the carrier.

The activation of predetermined areas comprises in particular cleaving a protective group off the carrier itself or off materials or building blocks thereof which are bound on said carrier.

The illumination matrix facilitates a flexible control of the time course of the exposure so that the exposure may take place at a rate in the range of from, for example, 1/10000 to 1000, in particular 1/10 to 100 light patterns per second.

According to a preferred variation of the method, exposure of the carrier is monitored by a light sensor matrix, in particular a CCD matrix, and, where appropriate, controlled taking into account the information obtained by said monitoring. Preferably, the sensor matrix is arranged opposite to and facing the illumination matrix, with the carrier being positioned between illumination matrix and sensor matrix in order to make transmitted-light observation possible. Alternatively, the illumination matrix, carrier and sensor matrix may also be grouped in a reflected-light arrangement.

The sensor matrix may be used for carrying out automatic recognition and/or, where appropriate, calibration of the particular carrier used by means of an analysis unit connected after the sensor matrix.

A further development of the invention may provide for removing the materials synthesized on the carrier, in particular polymers such as nucleic acids, nucleic acid analogs and proteins in order to provide them for particular purposes. In this aspect, it is possible to make use of the method practically as a preparation method for biochemical materials. In this context, it may be provided for to remove the materials in different areas in successive steps and to use them as building blocks for further synthesis of polymers, in particular nucleic acid polymers.

Further aspects of the invention, in particular, an illumination matrix which can be controlled to generate an optionally adjustable exposure pattern as light source of a light-emission detector for detecting the optical behavior of a 2- or 3-dimensional test area provided with biologically or biochemically functional materials, the test area being preferably prepared in the light-emission detector.

A further aspect of the invention should be pointed out, according to which a controllable illumination matrix is used for exposing in a spatially resolved manner reaction carriers with cells/tissue sections, in order to carry out exposure-dependent manipulations (light-sensitive processes such as photosynthesis, manipulation of retina preparations, light-dependent neuronal activity) or analyses (as 2D-FACS; cell-array, tissue-derived cell-array).

The invention further relates to a light-emission detector.

In this context, the illumination matrix or light source matrix is an illumination matrix which can be location-selectively controlled with respect to its optical transparency, in particular a light valve matrix, a reflection matrix or a self-luminous or self-emitting illumination matrix.

According to an embodiment of the light-emission detector, the illumination matrix is based on a light valve matrix (e.g. LCD matrix). In combination with a suitable light source, the light valve matrix makes the production of a highly parallel, high-resolution and location-specific exciting light source and inspection light source possible which, owing to its flexibility, opens up a multiplicity of possible applications. Light valve matrices are well advanced in their development due to their wide use in the electronic consumer goods sector and are therefore reliable, cheap and extremely small. As already illustrated, a possible application of this type of illumination matrix is to replace the relatively expensive photolithography (e.g. in the photoactivated oligo synthesis when preparing DNA chips) at relatively low resolutions, such as, for example, for simple Si chips or DNA chips.

The light sensor matrix can preferably be a CCD image recorder (CCD camera chip). If these two chips are arranged opposite to each other, then an extremely compact, highly parallel excitation, inspection and detection unit is obtained for an even larger number of applications. The two-dimensional light-emission detection unit develops its enormous potential in particular due to the intelligent interaction of two-dimensional control and two-dimensional readout. Here, the power of modern computers and software systems provides enormous potential for application and development, and both hardware and software can be based on the available systems for utilizing the light valve matrix (e.g. LCD) as man/machine interface. In applications using a combination of light source and detector, the intensity sensitivity (e.g. 264 to 4096 or to several 100 000 levels for CMOS CCDs) and the color (i.e. wavelength) distinction in the CCD chip (e.g. peak filters for red, green and blue or other colors, depending on the filters in front of the pixels) are suitable for two-dimensional spectroscopy. An object or other test samples to be studied/analyzed/excited or otherwise specifically illuminated with light and synchronously screened for light emissions is introduced onto or into the carrier between illumination matrix and light sensor matrix. A kind of sandwich structure composed of illumination matrix, carrier or test object and light sensor matrix is created. The distance between the illumination matrix and the test object and likewise between the test object and the light sensor matrix chip should preferably be minimal in order to minimize the deviation (scattering) of light from the relevant pixel of the illumination matrix to the opposite pixel of the light sensor matrix.

During the synthesis steps, the light-emission detector also serves as a detector, for example, for movements of fluids and allows integrated quality control or process control. This has a positive effect on quality and use of resources and reduces the reject rate. If no process monitoring during synthesis is needed and detection is carried out in a separate system, it is also possible to replace the light sensor matrix with a temperature control unit, for example.

The arrangement of a highly parallel illumination matrix and a highly parallel light sensor matrix creates a widely usable, novel inspection unit which may also be denoted as a massive parallel light barrier which, if necessary, additionally includes the advantages of quantitative and qualitative excitation and measurement. Another specific feature is the possible use of light of different colors (different wavelengths). In the case of a light valve matrix, it is possible, for example, to determine the excitation wavelength fundamentally by specifically using the appropriate background illumination of the light valve matrix.

Another strength of the light-emission detector is the almost endless possibilities which result from combining specific excitation with specific detection in conjunction with modern supercomputers for control and signal analysis. Thereby a new technology platform is created, especially for optical detection methods. Tuning of individual luminous spots in combination with CCD detection and suitable algorithms for the signal analysis ought to make very small changes in individual points of measurement in a light-emission detector possible. In DNA analysis, for example, detecting a hybridization directly in a reaction area would be conceivable.

In relation to image processing and to controlling the system components of the light-emission detector, it is possible, where appropriate, to make use of hardware and software tools. Examples are graphic cards, video cards and the appropriate software.

Compared to conventional photolithographic systems, the light-emission detector provides the possibility of extreme miniaturization with simultaneous functional integration when used as synthesis and analysis system (ISA system), in particular when using a light valve matrix, a reflection matrix, a diode array or a laser array as illumination matrix and a CCD image converter as light sensor matrix.

Particularly interesting applications of a light-emission detector of the invention are discussed briefly in the following:

Preparation of an opto-fluidic reaction carrier. In this connection, the light-emission detector of the invention is suitable in particular also for preparing a carrier for analyte determination methods which contains a multiplicity of channels, in particular capillary channels, in which a multiplicity of different receptors has been immobilized or is to be immobilized. Such a carrier is described, for example, in DE 198 39 256.7 (see priority document DE 198 39 256.7 for the present application). To prepare such a carrier, a carrier body having a multiplicity of channels is provided. Liquid which contains receptors or receptor building blocks is passed through the channels of the carrier body and receptors or receptor building blocks are immobilized in a location- or/and time-specific manner at in each case predetermined positions in the channels. Immobilizing can take place in the light-emission detector of the invention through exposure by means of the illumination matrix. A receptor can be synthesized on the carrier body by a plurality of successive immobilization steps of receptor building blocks.

As mentioned, photoactivation takes place at each step directly through the illumination matrix. In the case of using an LCD as illumination matrix, the wavelength of about 365 nm required for this process cannot be reached, unless the LCD has been designed as SPD.

It is conceivable that the user generates his highly parallel reaction carriers himself and uses them directly. He simply downloads the required data (DNA sequences) from a CD-ROM or from the Internet and generates in the light-emission detector (structure analogous to an external disk or CD-ROM drive) his individual DNA chip, moistens it subsequently with the sample and reads out the signals.

If, for example, every second pixel in this arrangement is used for photoactivation, then the pixels in between which are located within a capillary (microchannel in a reaction carrier) of the at least in some areas essentially transparent carrier body can be used for permanent process control. Thus, for example, the inflow of an air bubble between two fluids in a capillary can be followed individually and dynamically. Coloring the carrier fluids for G, A, C and T is also conceivable so that it would become possible to check the presence of the correct oligonucleotides and a color change could signal a contamination. During the subsequent detection, in turn a location-specific and, if necessary, even color-specific light excitation could take place. This leads to entirely new possibilities for detection methods which are at present not yet available.

By means of the light-emission detector it is further possible to monitor flow processes in the capillaries in a glass or plastic chip as carrier body both during production, that is to say oligo synthesis, and during analysis. For this it is possible, for example, to use air bubbles for cleaning between two fluids in the capillaries, or coloring of the individual fluids.

The illumination matrix may serve for the light-induced removal of protective groups during the synthesis of DNA oligos on the chip (carrier body) with, for example, an exposure wavelength of 365 nm. The required power is 14 mW per $cm^2$, for example. Eventually, further developments in chemical synthesis are also possible which utilize different wavelengths, for example.

The light-emission detector of the invention may likewise carry out detection of the test reaction for analyte determination methods in the carrier. If detection is carried out by fluorescent labels, the background illumination, where appropriate, would have to be changed for this purpose (automatically possible). Where appropriate, novel detection methods are also employed which only the extremely flexible individual illumination and detection of the individual points of measurement make possible.

In a preferred embodiment, the detection method for determining an analyte using a reaction carrier coated with biologically or biochemically functional materials includes the following steps:

(a) providing a reaction carrier having a multiplicity of different location-specifically bound or chemically functional materials, (b) adding a, where appropriate prepared, sample containing the analyte(s) to be determined, contacting the sample with the reaction carrier under conditions in which the analyte(s) to be determined bind(s) to the carrier-bound materials (receptors) and, where appropriate, subsequently washing the reaction carrier, and (d) optically analyzing the reaction areas in backlight or transmitted light by means of illumination matrix and sensor matrix.

The analyte determination steps (a) to (c) may be integrated into the synthesis process so that the analysis is carried out immediately after finishing the synthesis. This facilitates using the results from the analysis of a previous synthesis cycle for selecting the necessary carrier-bound materials for the reaction areas in the subsequent reaction carrier. It is then possible to continue the method with step (a), since the result from the analysis may require new selection of the materials bound in the reaction areas.

Another possible application for a light-emission detector of the invention relates to the incorporation into a method for determining a multiplicity of analytes in a sample as is described in the German patent application 198 39 255.9 (see priority document DE 198 39 255.9 for the present application). Said method for determining a multiplicity of analytes in a sample includes the steps:
(a) contacting the sample with
  (i) a multiplicity of microparticle types, each type being suitable for detecting particular analytes and having a particular coding which is optically distinguishable from other types, and
  (ii) a multiplicity of soluble, analyte-specific detection reagents which carry a signal-emitting group or can bind to a signal-emitting group,
(b) subsequently applying the microparticles onto a carrier and
(c) determining the analytes by optical detection of the coding and the amount present or/and the absence of the signal-emitting groups on at least one type of individual microparticles on the carrier.

Suitable samples are in particular biological samples. The microparticles may be organic particles such as organic polymer lattices or inorganic particles such as magnetic particles, glass particles etc.

Each type of the preferably optically transparent microparticles has on its surface at least one immobilized, different, analyte-specific receptor. The microparticles are preferably color-coded. For each analyte to be determined, at least one soluble, analyte-specific detection reagent is used.

After applying the microparticles onto the carrier and inserting the carrier between the illumination matrix and the light sensor matrix, it is possible to determine a statistical or dynamic arrangement of the microparticles on the carrier by means of the light-emission detector, specifically by image detection by means of the light sensor matrix.

The microparticles which are also called beads or smart beads represent in their entirety a multiplicity of points of measurement. The light-emission detector facilitates not only localization and assignment of the individual beads in their arrangement on the carrier by means of the light sensor matrix, but moreover also a likewise localized illumination. In this combination, the light-emission detector is therefore particularly suitable for localizing and identifying parts of the carrier, also called fractal chip, and for delivering the necessary data using the appropriate software in order to prepare the fractal chip with high precision. The principle of this structure and the comprehensive access through illumination and detection should keep the error rate extremely low.

The light-emission detector can monitor the flow processes of the smart beads in a fractal chip during analysis.

Reading out the information from a smart bead array should take place in the light-emission detector, with the exciting light source, i.e. the illumination matrix, being located directly above the smart bead array and the light source matrix directly below the fractal chip with the smart bead array. This most compact construction minimizes the light paths and thus also the required light intensity as well as superposition effects of neighboring smart beads. The use of complicated, bulky, light-absorbing and expensive optics can be dispensed with, both on the excitation and the detection sides.

Another variation is a vertical orientation of the chip so that gravitational forces can also be utilized for loading and unloading the chip with the smart beads.

The sensor matrix can again be a CCD chip, for example. If, on such a CCD area of 25×37 mm with 2000×3000 color pixels, microparticles (smart beads) of 60 μm in diameter are arranged for direct detection, then at least 200,000 microparticles (smart beads) are obtained. Each microparticle covers approx. 120 squared color pixels with edges of 5-10 μm in length. This produces 30-40 color signals or 120 black and white signals per smart bead with a digital light intensity grading of 256 to 4096 (depending on the CCD chip) discrete brightness levels for each black and white pixel. Thus, in any case, a sufficient amount of data is present for a statistical verification of the signals.

The limit of the maximum number of synchronously detectable, differently color-coded smart beads is determined by the possibility of specific codability (chemical limit of reproducible color generation) of the smart beads and also by the possibility of optical detection of the color differences using a CCD chip. If the 256 intensity levels per color (RGB minimum requirement) are divided into 10 levels, then $25^3$=15,625 possible colors are obtained which can be detected. Extending the number of color classes using further color filters can increase further the number of detectable colors. Using quadruple color filters (e.g. RGB and magenta) in front of the above-described CCD chip would make it possible to detect theoretically 25×$25^3$=390,625 colors, with only approx. 30 quadruple color pixels left, of course. Owing to great advances in CCD technology, the listed numbers only describe the minimum standard in this technique. New chips already have a color depth of 12 bits (4096) and the first prototypes already have 81 million pixels over the same area. This results in a large growth potential also for the described application of CCD chip technology, and the parallel detection of $10^6$ individual smart beads is technically feasible.

According to a variation, it may be provided for an optical gate to be provided between smart bead array (fractal chip) and CCD camera chip.

According to another variation, it may be provided for optical elements, in particular imaging elements to be present between the smart bead array (fractal chip) and the CCD camera chip.

Applying the light-emission detector to high throughput screening (HTS) equipment would make it possible to construct in parallel any number of light-emission detector units or to integrate them into one apparatus in a modular way. Providing the oligos and also the washing liquid and the prepared sample is again a question of the embodiments. Here, numerous possibilities are available, from providing in the analysis apparatus to providing the exactly required amount directly in the reaction carrier to which just the sample, for example after PCR, is added. Integrating the sample preparation into the carrier chip is also conceivable, of course. In one variation, the fluids are driven into the appropriate capillaries only by capillary forces. For the individual steps, only the integrated valve has to be switched by a switching motor in the apparatus (e.g. externally by a micromotor or a piezoelectric drive, if the light-emission detector is to be miniaturized accordingly). If the individual containers or cavities in the chip were only closed with a foil or membrane or an appropriate lid, it would be possible in the case of insufficient capillary force to achieve a pumping function by applying pressure from the top.

One possible use of a light-emission detector of the invention could be the monitoring of slow flow processes in thin layer chromatography (TLC). Here, color labeling of the migration for the detection may, where appropriate, be dispensed with and a direct "in situ" control by the compact and cost-effective light-emission detector may be carried out instead.

A light-emission detector of the invention may also be used as inspection unit etc. in microsystem technology.

Regarding the use of the light-emission detector for analyte determination in biochips, it should be furthermore noted, that from using CCD detection a lens-less signal detection should be expected which can distinguish at least three separate wavelength peaks (colors: red, green, blue) and 64 intensity levels.

Integrating the differentially locatable exciting light source as illumination matrix will allow a plurality of excitation wavelengths (at least three, corresponding to the color scheme in monitors), so that using different fluorescent labels is possible without problems.

Another possible application for a light-emission detector of the invention is cytometry and the studying of other sufficiently small biological objects. The light-emission detector generally monitors a 2D matrix by localized light barriers, the emission width and high sensitivity and wavelength-dependent detection making the use of spectrometic principles possible.

A matrix of this type is therefore excellently suited for studying particles which are located in a liquid medium between "detector" and "analyzer".

An interesting application is the studying of whole cells as "particles". In contrast to a cytometry carried out in a 1D capillary, parallel classification of the cells according to their optically detectable parameters takes place in this case.

Determination according to size, optical properties such as fluorescence (after appropriate labeling using specific or nonspecific stains, for example antibody and lipophilic stain, respectively) or movement, for example in the case of macrophages, pathogenic or other single cell organisms or the like, is conceivable. The studying of sufficiently small multicellular organisms is possible too, for example a complete *C. elegans* population under certain experimental conditions.

Another field of application for a light-emission detector of the invention is provided by gel electrophoresis. In this case it is possible to monitor and analyze online the gel electrophoretic separation of biological test material, for example of DNA in agarose gels, by means of a light-emission detector, if electrophoresis chamber and light-emission detector are integrated accordingly. The user would be able to follow the separation, for example, via the monitor.

This would facilitate the analysis at the earliest time of the separation, which possibly results in an enormous time saving. The whole equipment could probably be designed distinctly smaller than is the case at the moment, owing to the sensitive and high-resolution light-emission detector, since most gel electrophoresis experiments are primarily evaluated by naked eye, and only secondarily a small part of separations is analyzed under a scanner. Said minimization results in improved cooling, which in turn facilitates higher voltage and thus quicker separation. Thus, further acceleration of the process is conceivable and overall great time savings are possible (compared to capillary electrophoresis, acceleration by a factor of 10 is quite realistic, with reduced consumption of material and analyte).

A possible extension is the automatic removal of material from the electrophoresis gel measured online, for example by a connected mini-robot/computer-controlled apparatus.

Some aspects of the invention are illustrated in the following, with respect to the figures. FIGS. 1-5 depict diagrams of different exemplary embodiments for devices for preparing/manipulating/studying a carrier (biochip) coated with biologically or chemically functional materials. FIG. 6 depicts a cross section of a part of a carrier with integrated illumination matrix.

Figure 7:
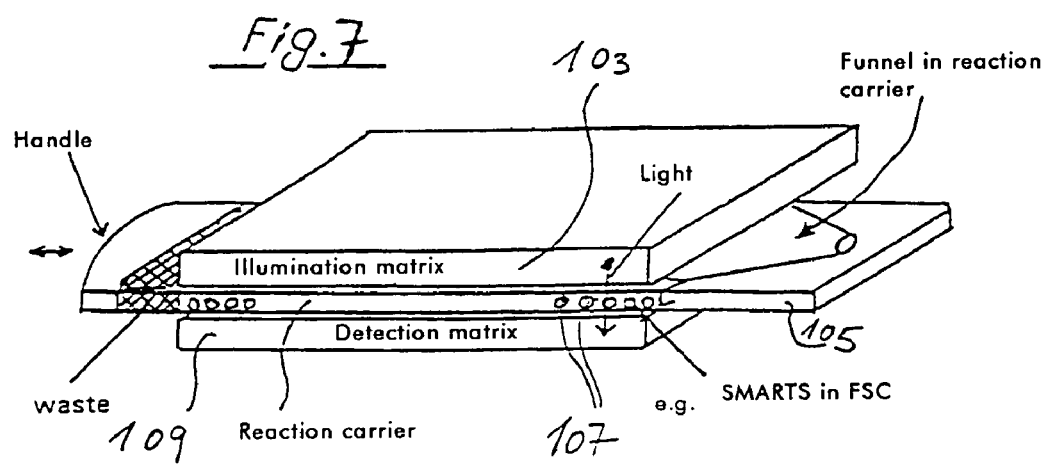
FIG. 7 is a simplified diagram of a light-emission detector in the form of a sandwich structure composed of a light valve matrix, transparent sample carrier with sample material and CCD matrix.

FIG. 7 depicts in a highly diagrammatic way an exemplary embodiment of a light-emission detector of the invention.

FIGS. 8 to 11 depict diagrams of devices of the invention which have self-luminous illumination matrices.

FIG. 1 depicts a first embodiment of an arrangement for preparing a biochip or/and for manipulating or/and for studying biologically or biochemically functional materials immobilized thereon.

The arrangement according to FIG. 1 can be conceptually divided into three groups of functional modules or system modules 2, 4, 6. The system module 2, also called below programmable light source matrix, includes at least one light source 8, at least one illumination matrix 10 which can be controlled to generate an optionally adjustable exposure pattern, and a control computer 12 which may be, for example, a programmable single chip microprocessor which is able to communicate, if required, with an external computer via an appropriate interface and which serves to control the illumination matrix 10 using an appropriate programme. Alternatively, the illumination matrix can be controlled from an external computer, for example personal computer. The system module 2 may further include optical elements 11, 14 which may be lenses, apertures, masks or the like and which are arranged for possible exchange where appropriate.

The second system module 4 is the exchangeable carrier or biochip which is to be exposed by the programmable light source matrix 2. The third system module 6 is a light detection unit which preferably includes a matrix made of light sensors 16. The matrix 16 is preferably an in particular color-capable CCD sensor chip which can be used for spectrally resolved and intensity-resolved, location-selective measurements. Where appropriate, the system module 6 may also contain optical elements 18 such as lenses, apertures, masks or the like.

The light sensor matrix 16 is arranged opposite and facing the illumination matrix 10, the carrier 4 being located in the (transmitted) light path between the illumination matrix 10 and the light sensor matrix 16.

In the case of the example according to FIG. 1, the illumination matrix 10 is an electronically controllable optical component whose transparency can be controlled with spatial resolution according to the resolution of the matrix, i.e. the arrangement and size of the matrix elements which form the matrix and which can be specifically controlled; the transparency can be switched preferably between two states, namely the essentially opaque state and a state of maximum transparency for the light of the light source 8. The illumination matrix 10 therefore can be considered as an electronically adjustable mask in a transmitted light arrangement. Depending on the control by the control computer 12, the illumination matrix 10 generates an exposure pattern which is used for exposing the carrier 4 location-selectively. The illumination matrix 10 used in the arrangement according to FIG. 1 is preferably a light valve matrix (LCD matrix with SPD filling). It is in principle also possible to use other light valve arrangements which can be controlled with spatial resolution, for example microplates, microsliders, etc., in order to realize an illumination matrix 10 of the kind depicted in FIG. 1.

The detection module 6 may be connected to the computer 12 or, where appropriate, to an external computer, for example personal computer, to control said module and to process the measurement information it provides.

The system modules 2 and 6 are preferably arranged on a shared holder which is not shown in FIG. 1, and they can be, where appropriate, adjusted relative to one another. The holder further has a sliding guide or the like by means of which the exchangeable carriers 4 can be introduced in each case into the position according to FIG. 1 in a simple manner and can be removed again from said position for removal of the appropriate carrier 4.

The arrangement according to FIG. 1 can be used in the preferred manner to coat an appropriate carrier 4 location-selectively with biologically or biochemically functional materials. For this purpose, a carrier 4 is used which has a surface having photoactivatable groups. Examples of suitable carriers are i.a. given in the German patent application 198 39 256.7. The programmable light source matrix 2 is used to generate an exposure pattern on the carrier surface provided with photoactivatable groups, in order to activate the photoactivatable groups in predetermined areas which are exposed to the light of the light source 8 in accordance with the exposure pattern. Via the feed 20, appropriate reagents may be fed to the surface (in the example to an inner surface of the carrier), which contain the desired biologically or biochemically functional materials or building blocks for such materials which are then able to bind to the predetermined areas. 21 denotes a discharge tubing for the reagents.

The biologically or biochemically functional materials or building blocks may for their part be provided with photoactivatable groups which can be activated by area in a possible subsequent activation step in accordance with the chosen exposure pattern, in order to bind in a further binding step biologically or biochemically functional materials or building blocks for such materials corresponding to the reagents employed. Not listed above were possible washing steps to flush the reagents used last, prior to the respective next exposure step. Depending on the activation wavelength of the photoactivatable groups, the exchangeable light source 8 may be a particular radiation source emitting in the infrared range, in the visible range, in the ultraviolet range or/and in the X-ray range.

Exposure, washing and binding steps can be repeated in a specifically controlled manner in order to generate, for example, a high-density microarray of biomolecules such as, for example, DNA, RNA or PNA.

Applications of this type do not necessarily require the light detection module 6; it is, however, possible to utilize said module expediently for online quality control of the processes which are light-dependent and take place in or on the carrier 4, i.e., for example, for monitoring an in-situ synthesis of biomolecules for preparing a microarray. The light sensor matrix 16 facilitates monitoring with spatial resolution the light-dependent processes via optical signals.

The light detection module 6 may generally be used for graduating or calibrating the system prior to a synthesis or analysis or other reactions or manipulations on or in the carrier.

The light sensor matrix 16 may, where appropriate, also be used for type recognition in which, for example, a carrier or chip body assigned to particular applications is automatically detected and the reactions and settings during subsequent processes are automatically adjusted.

By using the optical elements 14, it is possible to focus the two-dimensional exposure pattern, where appropriate, in one or more particular planes in or on the reaction carrier. Shifting the focusing plane during a process is also conceivable.

Figure 2:
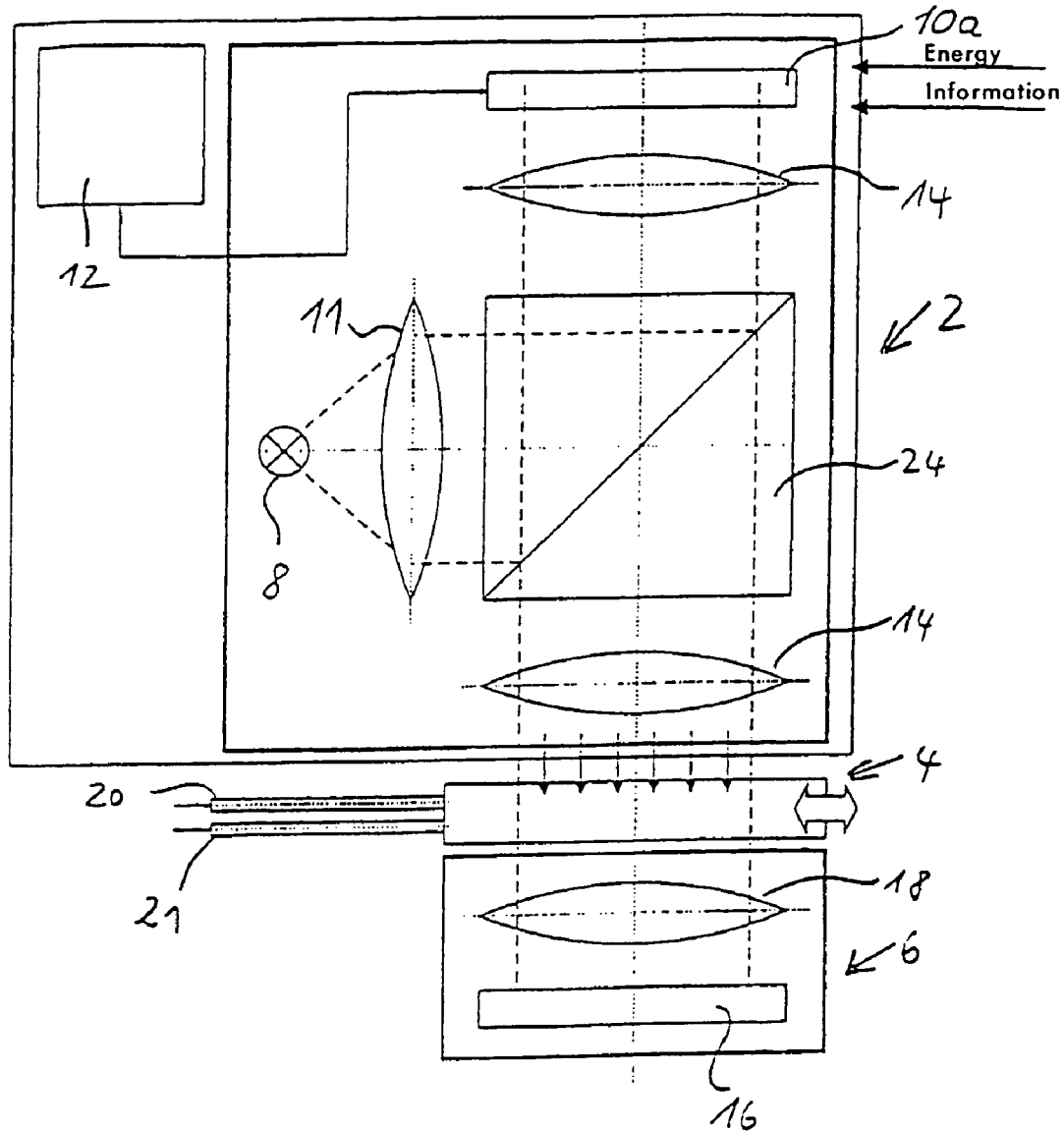
FIG. 2 is a diagram of an arrangement for preparing, studying and/or manipulating a reaction carrier.

FIG. 2 depicts a diagram of a second embodiment of an arrangement for preparing, studying and/or manipulating a reaction carrier. Elements in FIGS. 2-6 which correspond in their function to elements in FIG. 1 are marked with in each case corresponding indicators so that in this respect the description of the first exemplary embodiment can be referred to. In the embodiment according to FIG. 2, the illumination matrix provided for is an electronically controllable reflection matrix 10a. The electronically controllable reflection matrix 10a used may be, for example, a high-resolution surface light modulator with viscoelastic control layer and mirror layer. Such surface light modulators with viscoelastic control layers are illustrated, for example, in the data sheet entitled "Lichtmodulatoren mit viskoelastischen Steuerschichten" [Light modulators with viscoelastic control layers] which has been published by the Fraunhofer Institute for Microelectronic Circuits and Systems, D 01109 Dresden, Germany (information therefrom on pages 44-47 of the present application). Such a surface light modulator allows generation of an exposure pattern with spatial resolution for exposing the reaction carrier.

Alternatively, the electronically controllable reflection matrix 10a used may also be a surface light modulator with one or more micromechanical mirror arrays as is illustrated in the data sheet entitled "Lichtmodulatoren mit mikromechanischen Spiegelarrays" [Light modulators with micromechanical mirror arrays] which has been published by the Fraunhofer Institute for Microelectronic Circuits and Systems (information therefrom on pages 48-52 of the present application). Reflection surface light modulators have also been developed by Texas Instruments.

Very generally, such electronically controllable mirror matrices with CMOS 40V technology are very well suited to the requirements of the present invention, since they can be employed over a broad spectral range, in particular also in the UV range in order to generate the desired exposure patterns. This is not true for UV-sensitive mirror matrices with, for example, 5V technology.

Direction of the light path according to FIG. 2 additionally requires a light deflection element 24 which may be, for example, a partly transparent mirror which deflects the light coming from the light source 8 to the reflection matrix 10a and allows the light which is reflected back from the reflection matrix 10a to pass through downward to the reaction carrier 4 so that it is possible to utilize on the reaction carrier 4 or, where appropriate, in the reaction carrier 4 the exposure pattern generated in accordance with the control of the reflection matrix 10a for photoactivating, analyzing or manipulating biochemical processes.

Figure 3:
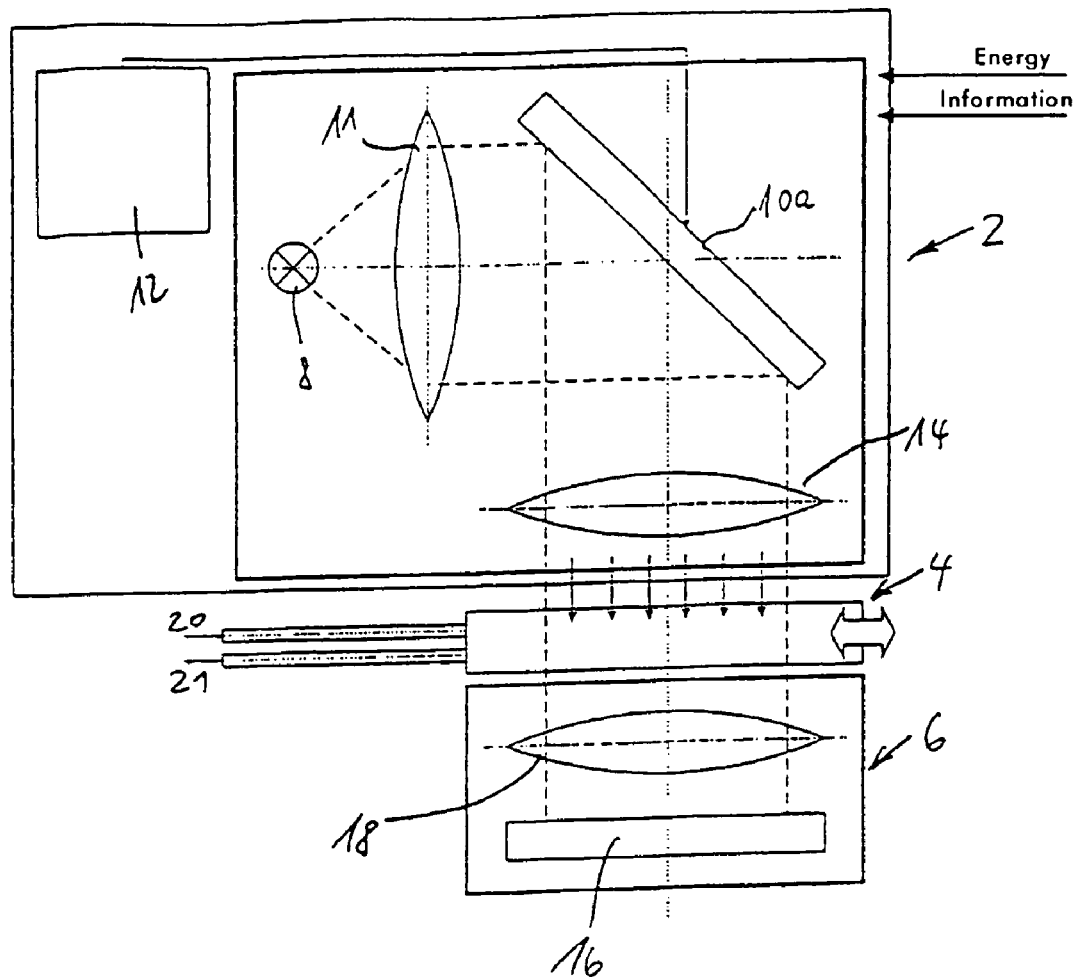
FIG. 3 is a diagram showing a variation of the arrangement in FIG. 2, with a light path lacking the deflection element shown in that Figure.
Figure 13:
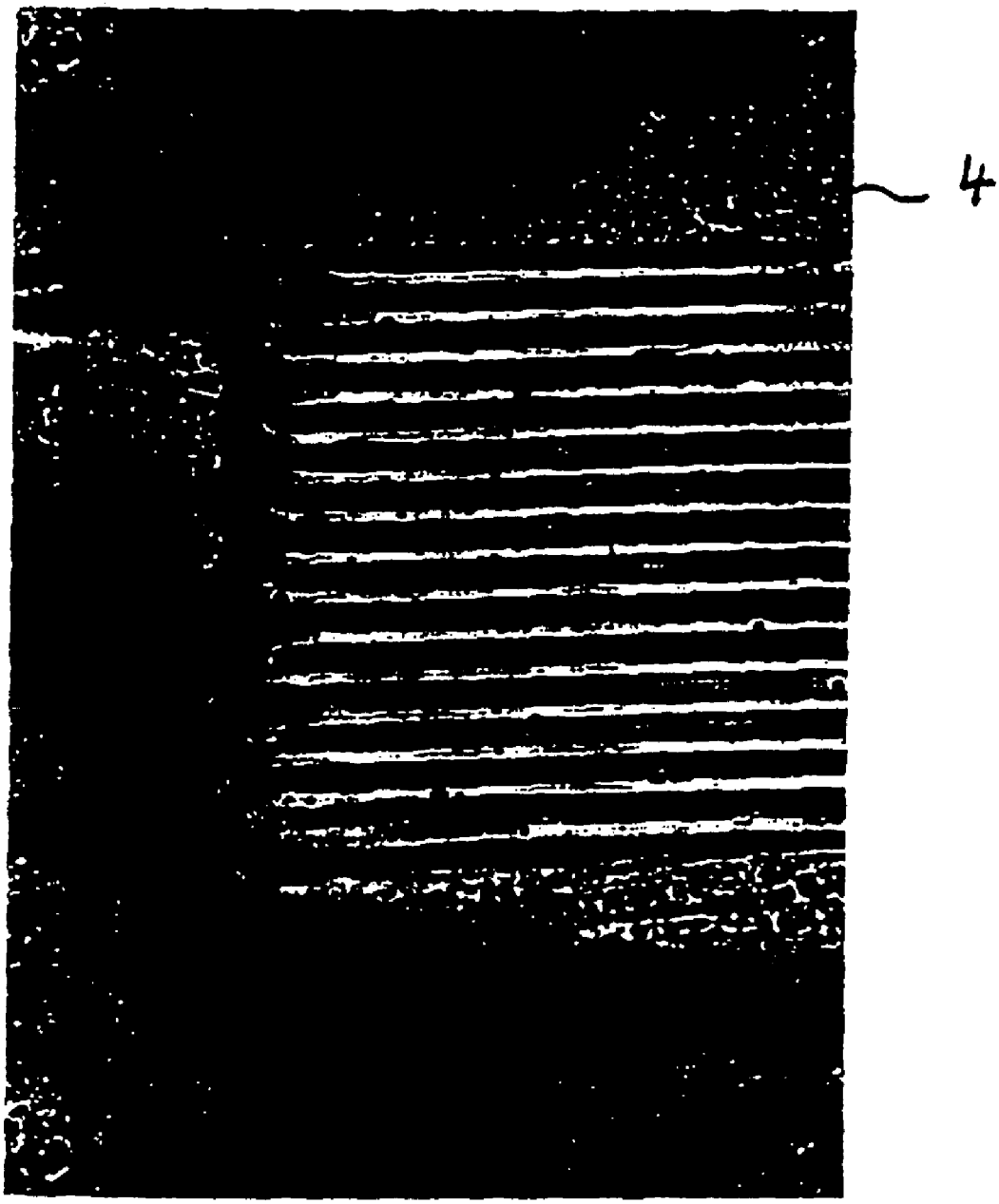
FIG. 13 depicts a carrier body.

FIG. 3 shows a variation of the embodiment according to FIG. 2, in which the embodiment of FIG. 3 has a light path for which the deflection element denoted as 24 in FIG. 2 can be dispensed with, since the controllable reflection matrix 10a is arranged such that it can deflect light coming from the light source 8 to the reaction carrier 4 in accordance with the chosen exposure pattern. When using a structure corresponding to the variation of FIG. 3, the image of a carrier with meandering channel is visible in FIG. 13. In this case, there are no optical elements whatsoever between carrier and CCD sensor, so this is a lens-less direct detection. The light source used in this case is a laser.

Figure 4:
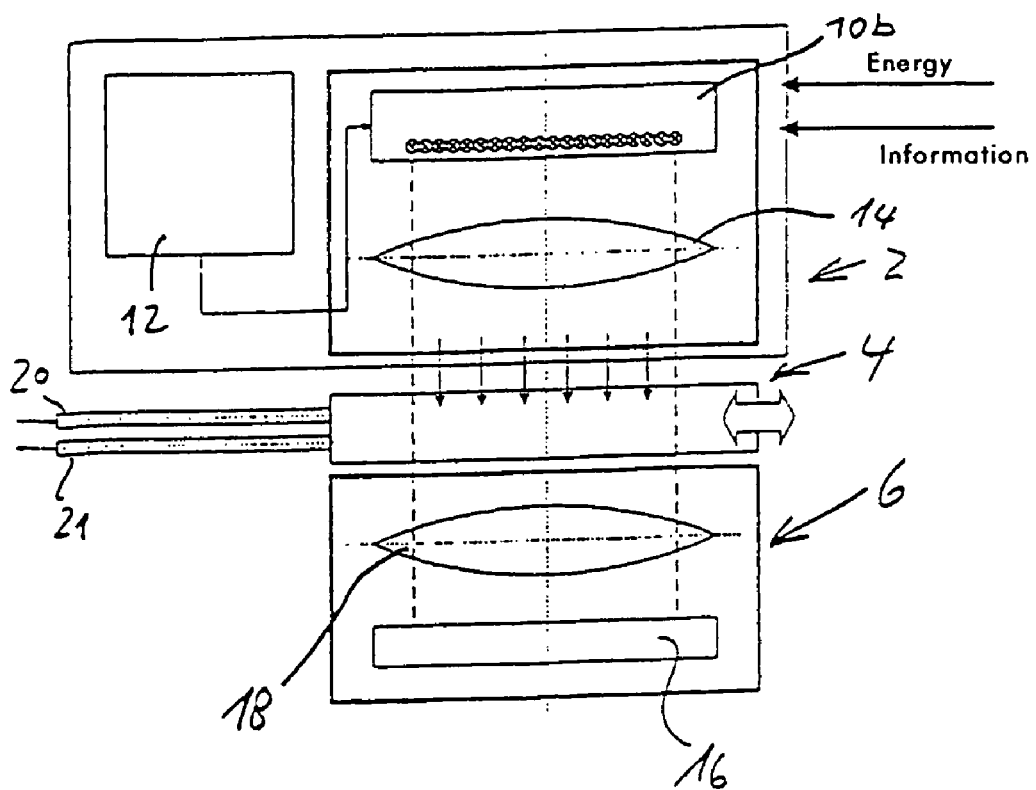
FIG. 4 is a diagram of a further embodiment of an arrangement for preparing, studying or/and manipulating a carrier.

FIG. 4 depicts a diagram of another embodiment of an arrangement for preparing, studying or/and manipulating a carrier of the present invention. In the embodiment according to FIG. 4, the illumination matrix used is a matrix arrangement 10b made of light sources, for example a microlaser array or a microdiode array. At the moment developments are taking place which are aimed at putting a multiplicity of microscopically small semiconductor lasers as tiny powerful light sources on a single chip. A controllable "light chip" of this type could be used as matrix 10b. Regarding literature on the background of the "light chips", the journals: Nature 3, 97, pp. 294-295, 1999 and MPG-Spiegel 4/98, pp. 13-17 may be referred to for example.

Figure 5:
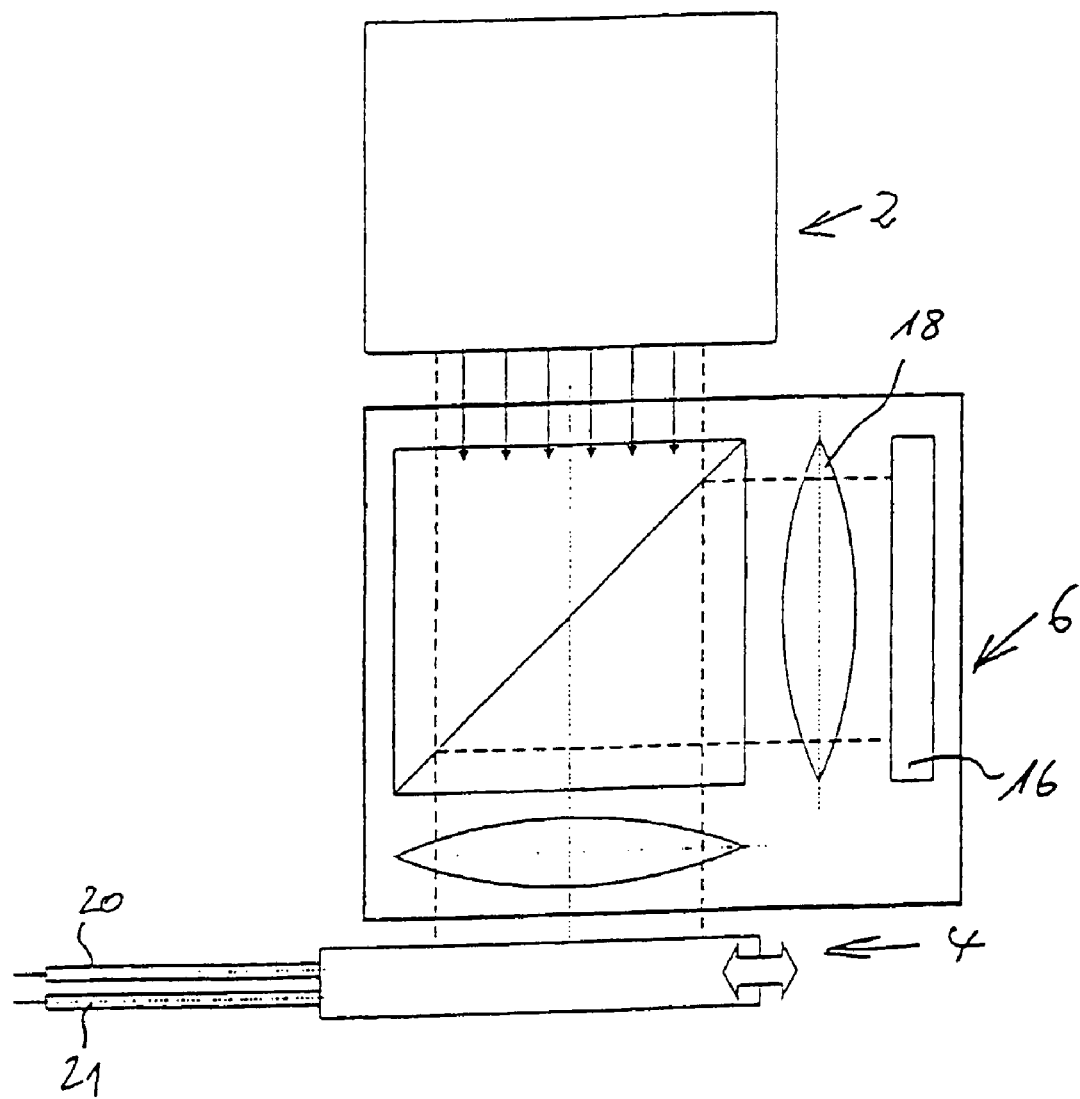
FIG. 5 is a diagram of an arrangement in which the detection module with sensor matrix is set up for reflected light or backlight observation of the reaction carrier.
Figure 6:
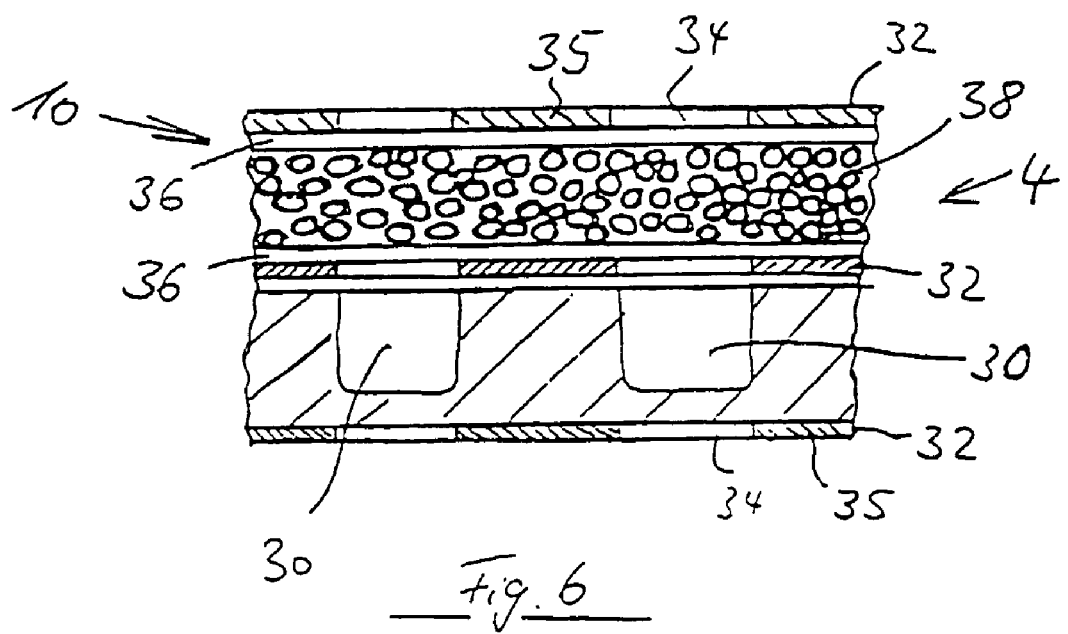
FIG. 6 shows a section through an embodiment of a carrier in which the illumination matrix is part of the carrier body.

FIG. 5 shows an arrangement in which the detection module 6 with sensor matrix 16 is set up for reflected light or backlight observation of the reaction carrier 4.

All arrangements according to FIGS. 1-5 can be used as light-emission detectors for detecting the optical behavior of a carrier test area provided with biologically or biochemically functional materials. This may take place in a manner as is disclosed in the German patent application 198 39 254.0.

FIG. 6 shows a section through an embodiment of a carrier 4 of the invention, said embodiment being distinguished by the illumination matrix 10 being part of the carrier body 4. In this case, the illumination matrix used is preferably a light valve matrix which can be disposed of together with its chip carrier 4, after the carrier is no longer used.

In the exemplary case of FIG. 6, the carrier body 4 has capillary channels 30 whose walls serve as preparation surface for the coating with biologically or biochemically functional materials. The channels 30 can be selectively charged with the appropriate reagents. The following details are detectable in FIG. 6: boundary layers 32 with transparent and nontransparent areas 34 and 35, respectively, transparent electrodes 36 with SPD particles (suspended particles) enclosed between and to be influenced by the electrodes 36, or alternatively liquid crystals 38.

FIG. 7 depicts a greatly simplified diagram of a light-emission detector of the invention in the form of a sandwich structure composed of light valve matrix 103 (two-dimensional liquid crystal exposure element), transparent sample carrier 105 with sample material 107 included therein and CCD matrix 109 (image recorder). The light valve matrix 103 and CCD matrix 109 can be controlled from a shared (not shown) control unit, for example in order to switch matrix elements of the light valve matrix and the CCD matrix assigned to one another into the active state simultaneously.

Figure 12:
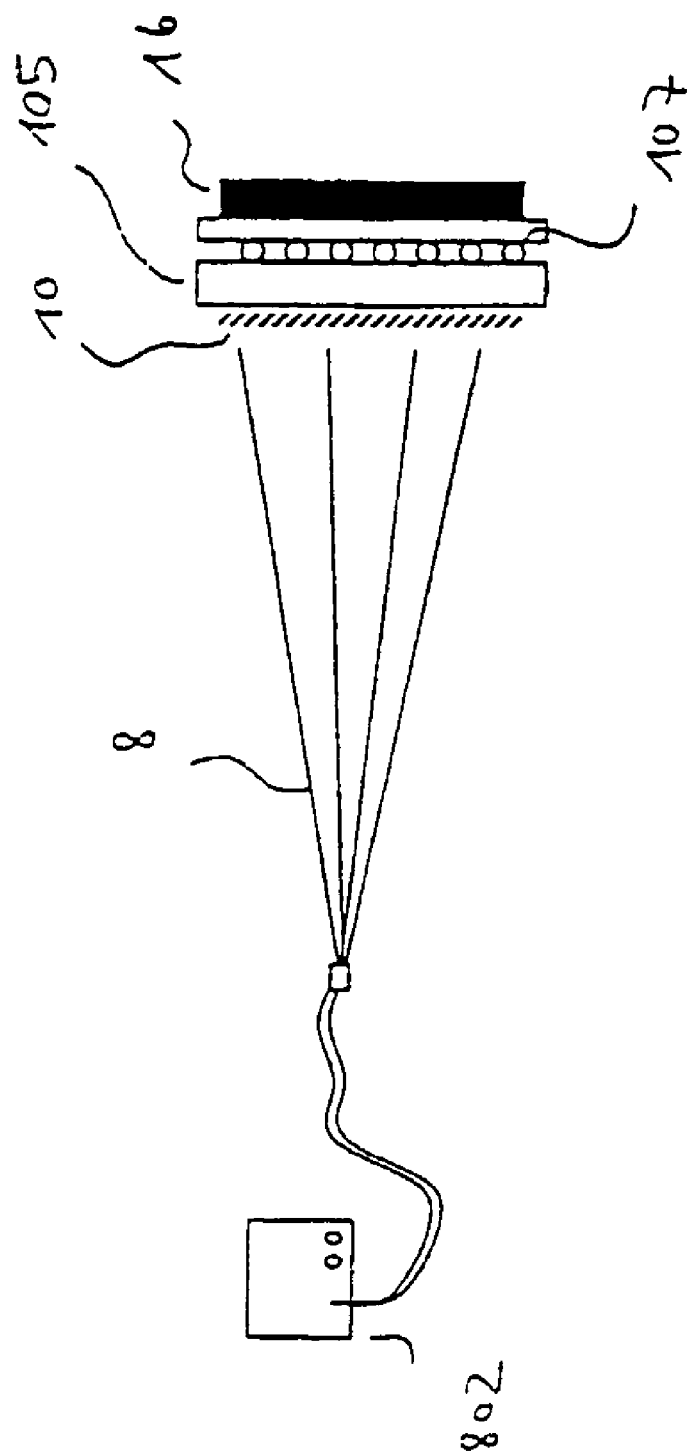
FIG. 12 shows an arrangement with a transparent carrier filled with colored microparticles.

The arrangement shown is suitable, for example, for measuring the optical absorption of the sample material 107 in the transparent carrier 105. The sample material 107 may be microparticles (smart beads), for example. Such an arrangement is shown in FIG. 12. Here, a commercially available Neubauer cell counting chamber as transparent carrier 105 has been filled with colored microparticles 107. When illuminating with a light source 8, consisting of a cold light source with fiber coupling-out and aperture (802), colored microparticles can be detected by the CCD sensor and the color can be determined by absorption (not visible in black and white). After labeling the microparticles with fluorophores, it is possible to detect said fluorophores in the same way by the CCDs sensor using a suitable light source.

Means for positioning the light valve matrix relative to the CCD matrix are not visible in FIG. 7. Said means could be, for example, means for tilting the light valve matrix 103 relative to the CCD matrix 109. Of course, it is possible to choose numerous other possibilities in order to position the light valve matrix 103 and the CCD matrix 109 in the correct position to one another and, where appropriate, to fix them to one another.

Figure 8:
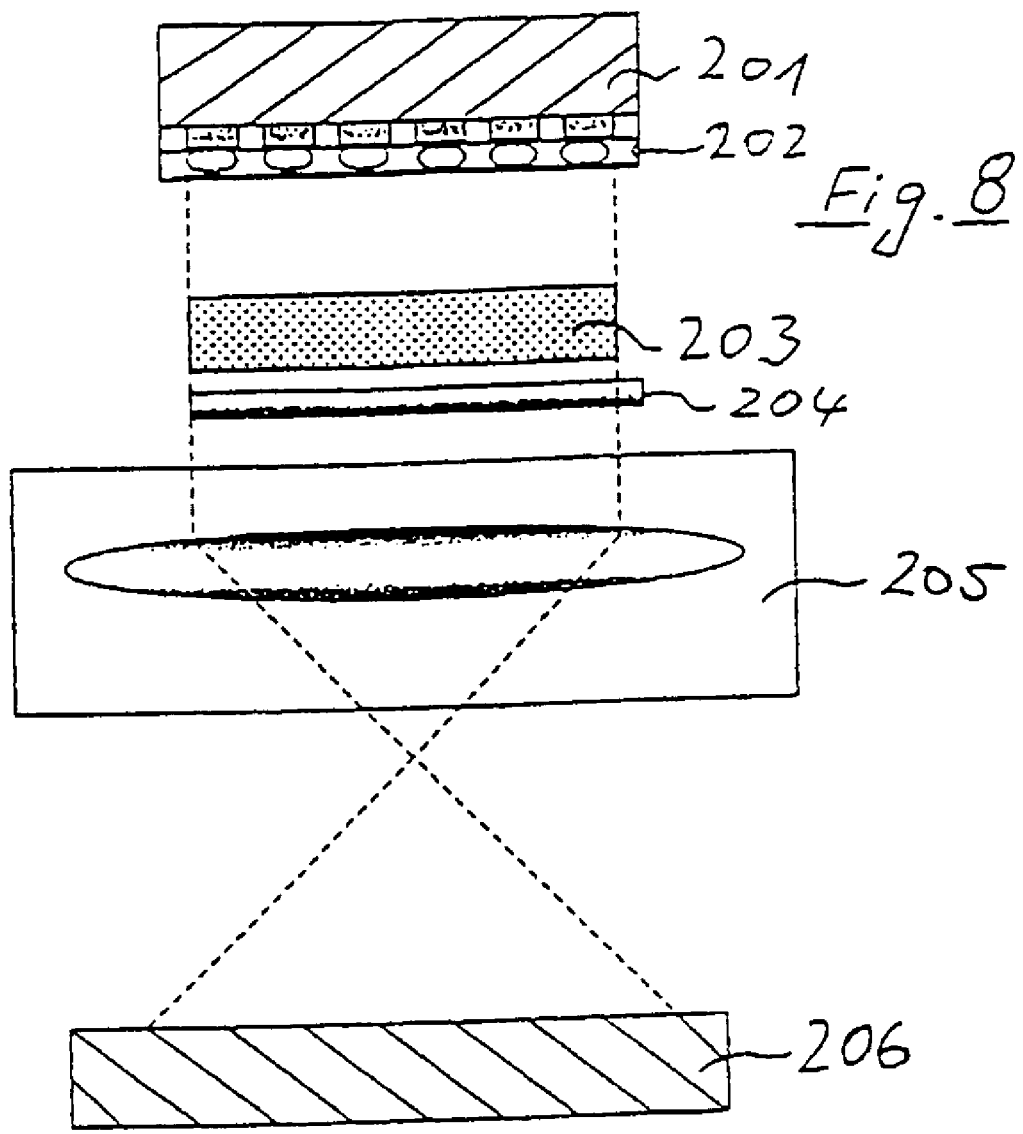
FIG. 8 depicts another arrangement for the spatially resolved photochemical synthesis of polymer probes on a carrier and/or for manipulating and/or studying immobilized, biological, biochemically functional materials.

FIG. 8 shows another arrangement for the spatially resolved photochemical synthesis of polymer probes on a carrier and/or for manipulating and/or studying immobilized, biological, biochemically functional materials. The arrangement according to FIG. 8 can be conceptually divided into the three functional modules 201, 203 and 206. In this connection, the system module 201 constitutes an illumination matrix, for example in the form of an LED matrix, which in a software-controlled manner generates an illumination pattern which can induce the spatially resolved photochemical synthesis of polymer probes in the carrier 203. Coupling the illumination pattern in the carrier 203 is carried out with the aid of the system component 202. Said system component may be, for example, a mechanical mask with an aperture for each LED matrix element. More suitable is the use of micro-optical elements such as microlenses, for example. Furthermore, said system component may also be a fused fiber optical taper which makes it possible to considerably reduce divergence of the light emitted from the individual light source elements. Opposite the carrier 203, an optical four-channel detector (preferably a CCD sensor or a CCD camera) is located on the exit side of the light. The working mode of said CCD camera is adjusted to the operation of the illumination matrix 201 with the aid of suitable hardware or software. For controlling, preference is given to using a personal computer which controls the illumination matrix and the CCD camera. Alternatively or additionally, a frequency generator may also be used for controlling and for electronically synchronizing the illumination matrix 201 and the, in this case, gated CCD chip 206 with one another. The latter embodiment will facilitate in particular fluorimetric detection of the analytes bound to the carrier 203 without it being necessary to introduce additional frequency-selective elements between the carrier 203 and the detector matrix 206. However, as has already been mentioned above, a precondition for this method is to be able to switch the individual elements of the illumination matrix on or off within a time range of a few nanoseconds. An alternative to this is an optical filter 204 which can facilitate spectral separation of the exciting light and the signal light in fluorimetric detection. When using a filter wheel 204, it is moreover possible to analyze simultaneously on the same carrier 203 analytes of different sample materials which have been labeled with fluorophores of distinctly different emission maxima. The location-selective reproduction of the signal light emitted from the carrier 203 on the detector matrix 206 may optionally be carried out using the component 205. Said component may either be an optical lens system or a fused fiber optic taper.

Figure 9:
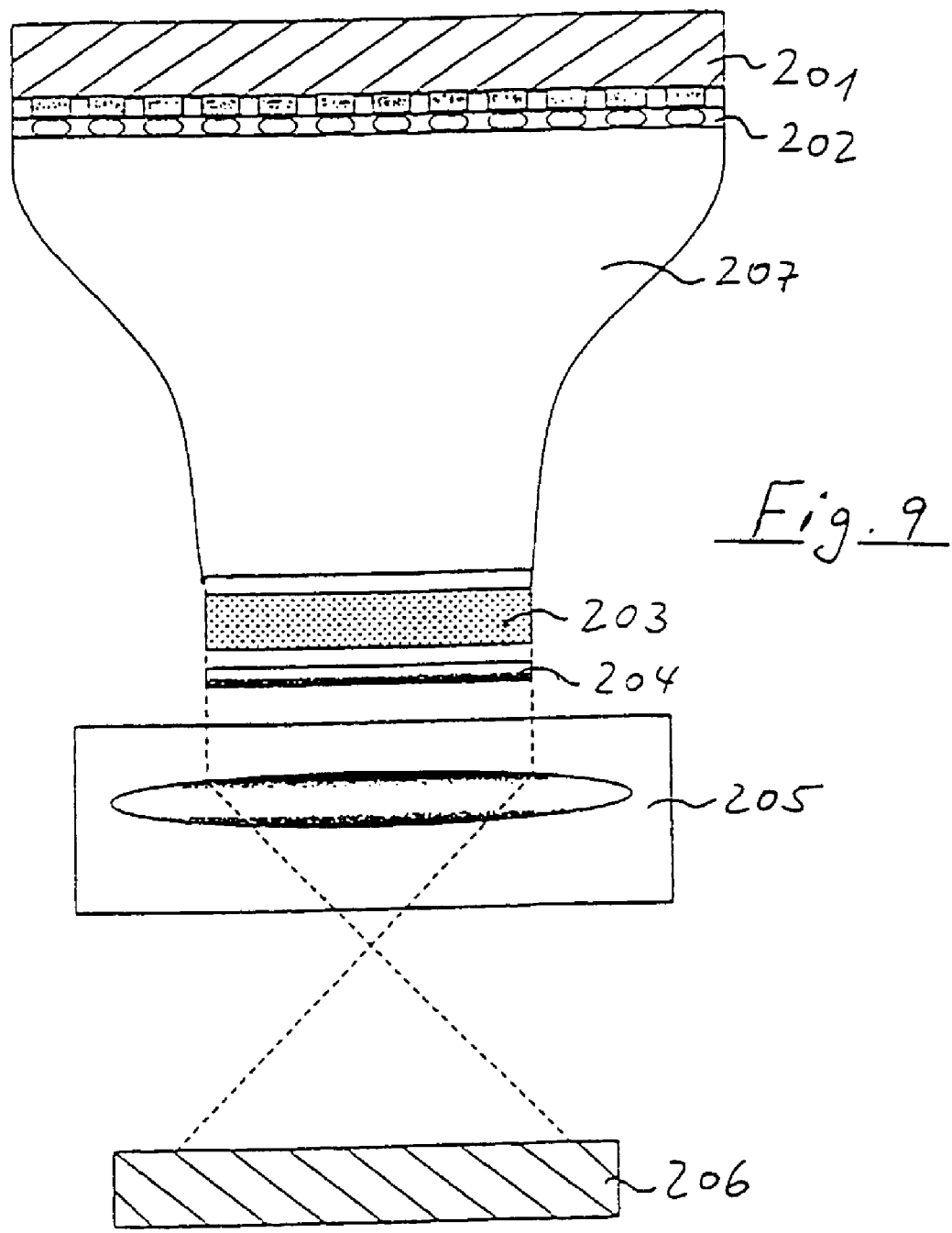
FIG. 9 shows an embodiment of a device in which the illumination pattern generated by the illumination matrix is a reduced size and the optical image is reduced by guiding the beam in a fused fiber optic taper.
Figure 11:
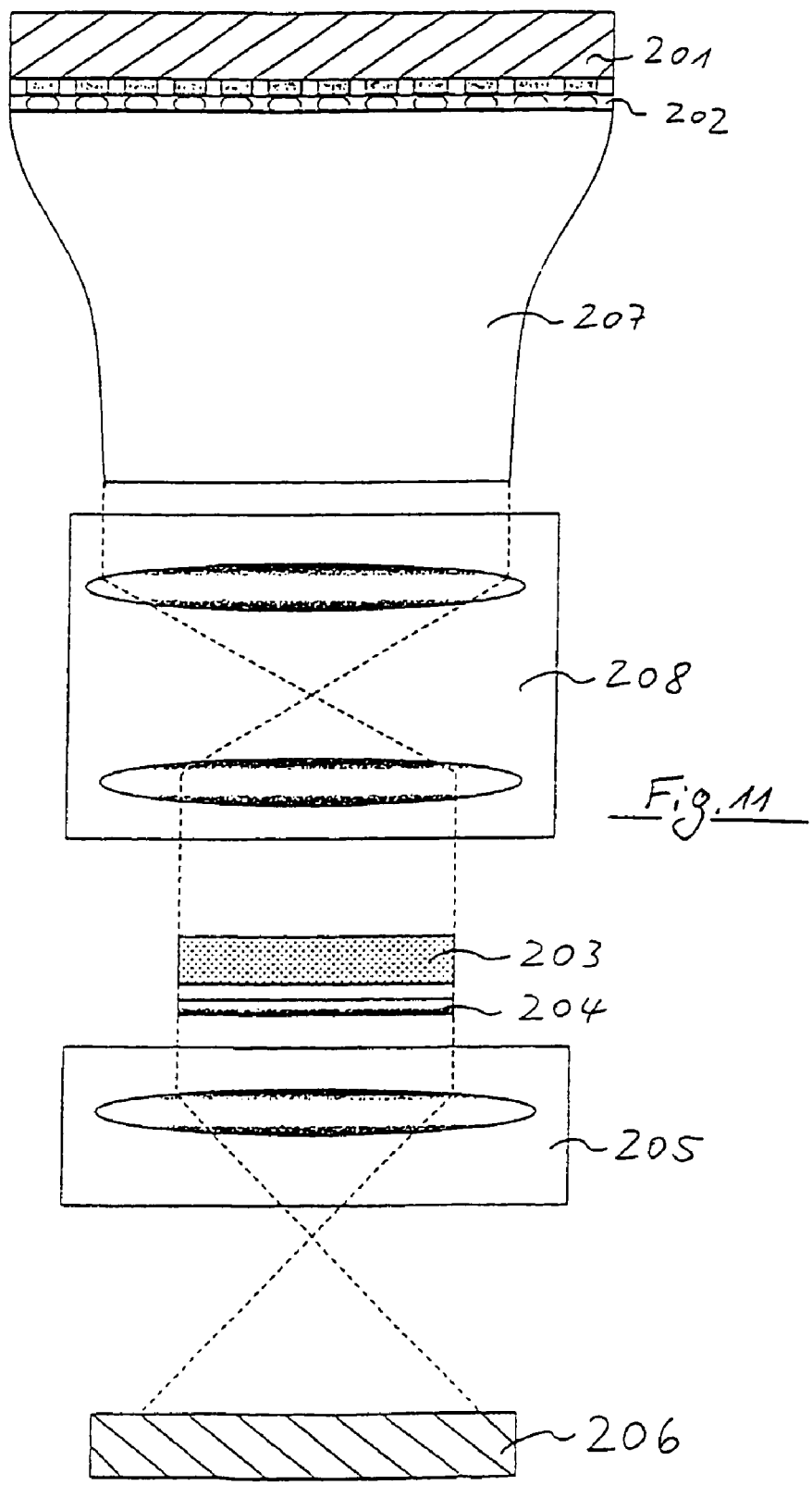
FIG. 11 shows an embodiment as for FIG. 9, but where the reduction is achieved using a fused fiber optic taper and an optical lens system.

FIGS. 9, 10 and 11 show further possible embodiments of a device of the invention. Common to all these embodiments is the reproduction of the illumination pattern generated by the illumination matrix 201 on the carrier 203 at a reduced size. Elements in FIGS. 9, 10 and 11 which correspond to the elements in FIG. 8 with respect to their function, are marked by in each case corresponding reference symbols so that in this matter the description of the exemplary embodiment according to FIG. 8 may be referred to. For the embodiment according to FIG. 9, the optical image is reduced by guiding the beam in a fused fiber optic taper 207, whereas in the exemplary embodiment according to FIG. 10 reduction is achieved using a suitable optical lens system 208. Both micro- and macrolens systems may be employed here. The exemplary embodiment depicted in FIG. 11 finally uses a combination of a fused fiber optic taper 207 and an optical lens system 208.

In summary, the following should also be noted regarding FIGS. 8-11. They show a device having a light source matrix, a micro-optical component and also reducing optics for light-controlled induction of spatially resolved chemical or biochemical syntheses in one reaction carrier. In the case of using an LED matrix as light source matrix, it has proved to be expedient, that no more than 75% of the light source matrix surface area is covered with LEDs.

It should be mentioned that one or more gaps between individual elements of the device may be filled with an optical fluid.

With respect to the inventive embodiment depicted in FIG. 3, FIG. 12 shows an arrangement including a transparent carrier 105, for example a commercially available Neubauer cell cell chamber which has been filled with colored microparticles 107. When illuminating with a light source 8, for example a cold light source with fiber coupling-out and aperture (802), the colored microparticles can be detected by the CCD sensor matrix (16) and the color can be determined by absorption. When labeling the microparticles with fluorophores, detection by the CCD sensor can be carried out in an analogous manner.

Figure 14:
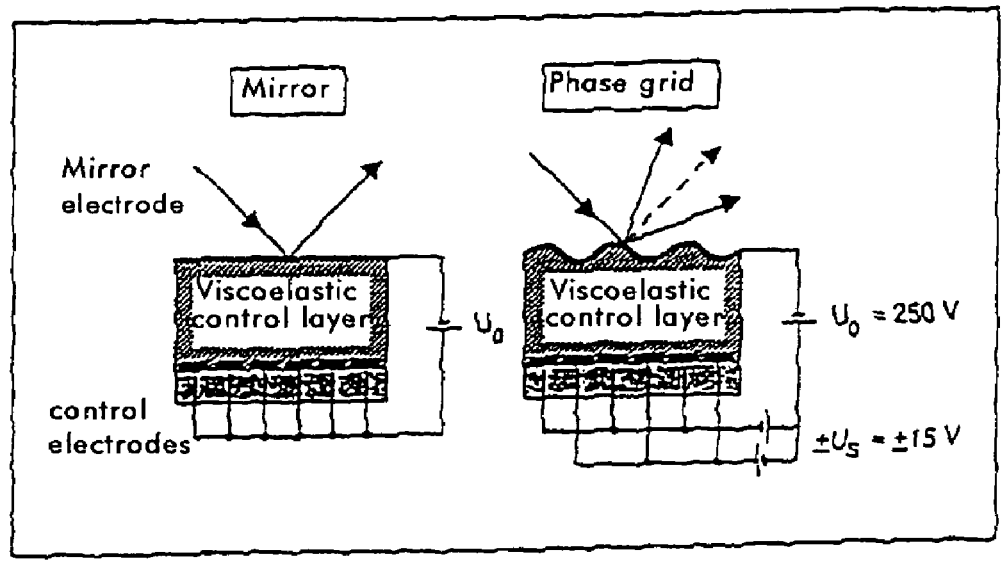
FIG. 14 is a diagram taken from the data sheet: "Lichtmodulatoren mit viskoelastischen Steuerschichten."
Figure 15:
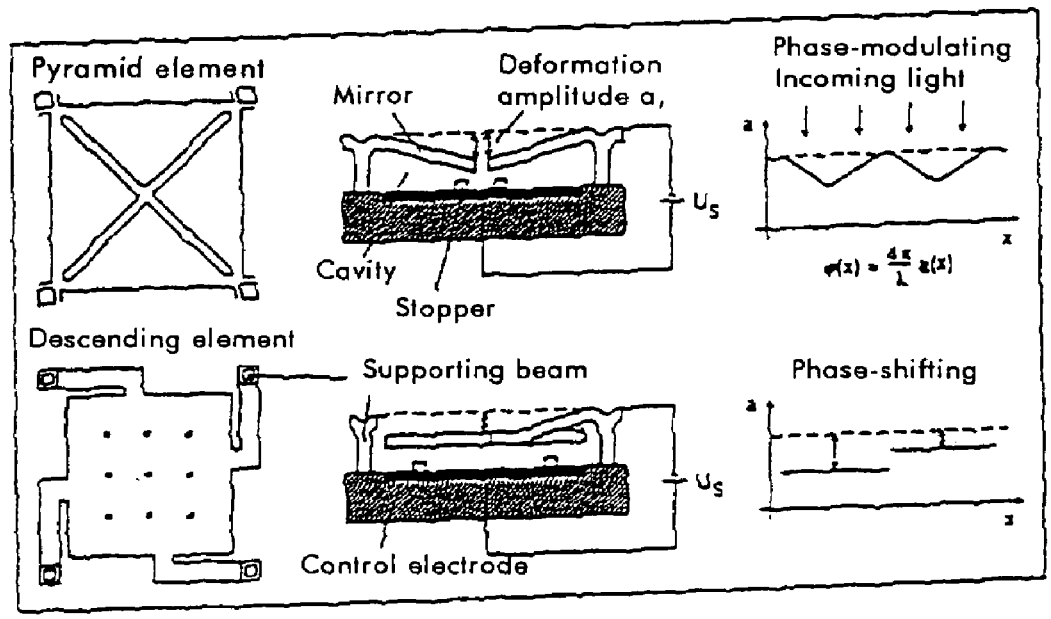
FIG. 15 is a diagram taken from the data sheet: "Lichtmodulatoren mit mikromechanischen Spiegelarrays."

FIGS. 14 and 15 were taken from the data sheets: "Lichtmodulatoren mit viskoelastischen Steuerschichten" [Light modulators with viscoelastic control layers] and "Lichtmodulatoren mit mikromechanischen Spiegelarrays" [Light modulators with micromechanical mirror arrays] of the Fraunhofer Institute for Microelectronic Circuits and Systems, IMS 1998 (therein in each case FIG. 1).

Information from the data sheet:

"Lichtmodulatoren mit viskoelastischen Steuerschichten" [Light modulators with viscoelastic control layers] by the Fraunhofer Institute for Microelectronic Circuits and Systems, IMS, D-01109 Dresden, Germany Features Viscoelastic control layers form a class of high-resolution surface light modulators (SLMs) with deformable mirror arrangements. They consist of an array of independently controllable control electrodes on an underlying active CMOS control matrix which is coated with a viscoelastic silicone gel. A thin aluminum layer is applied thereupon which forms a continuous mirror surface and has high reflectivity in the complete range from IR to far UV.

Operation Principle

FIG. 1 (depicted in FIG. 14 of the present application) shows diagrammatically the cross section of a viscoelastic control layer. To activate, a bias is applied between the mirror and the control electrodes which puts the arrangement in its entire area under mechanical pressure. The surface initially stays smooth and acts optically as a planar mirror. Only application of an additional control voltage with alternating polarity to neighboring control electrodes leads to a deformation owing to the changing electrical field strengths. Switching the polarity either for one or both spatial directions can generate either 1D or 2D sinusoidal deformation profiles.

FIG. 2 (of the IMS data sheet) shows in this connection the surface profiles measured for an embossed-engraved pattern. Optically, these deformation profiles are phase grids whose grid period is defined by the distance between the control electrodes. The incoming light undergoes a phase modulation corresponding to the differences in the optical path given by the mirror deformation. Choosing an appropriate deformation amplitude makes it possible to deflect nearly the entire amount of light into higher orders of deflection, whereas the light of non-addressed planar pixels only occupies the zero order.

In connection with a suitable optical system, it is then possible to achieve the situation where only light of non-addressed areas is let through and is projected into the focal plane as visible intensity pattern.

Viscoelastic control layers are therefore well suited to generating phase patterns for optical imaging applications. Using this technology, an SLM prototype working in binary mode with an active matrix of 1024×2048 pixels and 20×20 $\mu m^2$ pixel size was developed, with a specific high-voltage CMOS process being employed to facilitate control voltages of up to ±15 V.

FIG. 3 (of the IMS data sheet) shows in this connection the diagrammatic layout of the active control matrix. The operation of this prototype was successfully demonstrated in an application for fast direct laser exposure of sub-$\mu$ structures. Said prototype served to generate phase patterns from the CAD layout data of IC mask layers, which patterns were then converted into an intensity image for the photoresist structuring with the aid of the optical system.

At present, light modulators are being developed which allow 4-bit analog operation and graduation of the image field size in steps of 256 pixels for each direction.

Applications

Light modulators with viscoelastic control layers open up many new application possibilities:

Display Technology:
  Video and data projection
  Head-up displays

Information Technology:
  Optical image and data processing
  Optical storage

Production Technology:
  Mask-free direct writing
  Laser ablation and production

| Technical parameters | |
|---|---|
| Pixel size | >16 × 16 $\mu m^2$ |
| Pixel number | 256 × 256 . . . 1024 × 2048 |
| Profile | 1D, 2D sinusoidal |
| Modulation | phase-modulating |
| Operation | binary or 4-bit analog |
| Deformation amplitude | 0 . . . 150 nm |
| Control graph | nearly linear |
| Adjustment time | <2 ms |
| Data inputs | 16, 32, 48, 64 channels 4 bit, 5 V |
| Image frequency | 100 Hz . . . 500 Hz |
| Optical filling | 100% |
| Reflectivity | >90% IR . . . DUV) far UV |
| Construction technology | ceramic PGA shell |

User Evaluation Kit

In order to provide the possibility of testing all fundamental SLM functions in a user-specific environment, a user evaluation kit containing all components for user-specific image programming of the SLMs was developed.

SLM

| | |
|---|---|
| Pixel size | 16 × 16, 20 × 20, 24 × 24 µm² |
| Pixel number | 256 (160) × 256 |
| Pixel design | customer-specific |
| Operation | 4-bit analog |

SLM Board

| | |
|---|---|
| RAM | Storage of 2 images |
| Image frequency | 1 Hz (PC to RAM) |
| | 500 Hz (RAN to SLM) |
| I/O signals | Matrix Trigger, Matrix Ready |

Data Transfer
    via cable connection and digital I/O interface card for ISA slot on the PC Software
    Conversion of user image data from bitmap into SLM data format
    Control functions for data transfer
    Setting the control voltage level for 4-bit grayscale Requirements
    Windows-compatible PC
    Image pattern generation in bitmap data format, for example using Paintbrush
    Information from the data sheet:
    "Lichtmodulatoren mit mikromechanischen Spiegelarrays" [Light modulators with micromechanical mirror arrays] by the Fraunhofer Institute for Microelectronic Circuits and Systems, IMS, D-01109 Dresden, Germany Features
    Micromechanical mirror arrays form a class of high-resolution surface light modulators (SLMs) with deformable mirror arrangements. They consist of an array of independently controllable micromirrors which are produced on an underlying active matrix control circuit in a completely CMOS-compatible process using the methods of surface micromechanics. The process only needs three additional masks and thus allow easy adaptation of the light-modulating properties to a wide variety of application-specific requirements by merely changing the mirror architecture.

Operation Principle
    The micromirrors are produced using a sacrificial layer technique, so that hanging mirror elements are created above a cavity with underlying control electrode.
    Mirror and supporting beams consist to the same extent of aluminum in order to guarantee high reflectivity over a broad spectral range from IR to far UV.
    Activation takes place by applying a control voltage between mirror and control electrode so that the mirrors are deformed into the cavity due to the action of electrostatic forces. The differences in the optical path related thereto lead to a corresponding phase modulation in the incoming light. The deformation profile and thus the light-modulating properties depend in this context strongly on the particular mirror architecture. Here, three fundamental cases, phase-modulating, phase-shifting and light-deflecting, can be distinguished.
    From the multiplicity of possible pixel architectures, the two structures from FIG. 1 (depicted in FIG. 15 of the present application) have been studied in more detail.

In the first variation, electronic deformation of four identical mirror segments generates optical phase grids in which one pixel defines in each case one grid period with inverse pyramidal phase profile. Said variation is well suited to generate phase patterns for optical imaging applications.

The second variation consists of a mirror plate held by four arms, which mirror plate delivers, when electronically controlled, a planar piston-like descending movement and thus allows setting the phase of the incoming light for each pixel. This variation is well suited to phase front correction in adaptive optics.

Such micromirrors have already been built on passive matrices for studying the electromechanical properties (FIG. 2, 3 of the IMS data sheet). The measured graphs in FIG. 4 (of the IMS data sheet) show in this connection the typical deformation behavior. In the analog field, deformation increases almost quadratic with the control voltage. Above the so-called pull-in point the mirrors, however, owing to the co-coupling via the electric field, switch spontaneously to the fully extended state in which only binary operation is still possible. In order to set the mirrors finally back to an equilibrium between mechanical and electrical powers, an appropriate reduction of the control voltage is necessary.

Applications
    Light modulators with micromechanical mirrors open up a multiplicity of application possibilities:

Display Technology:
    Video and data projection
    Head-up displays

Information Technology:
    Optical image and data processing
    Optical storage Phase Front Correction of Adaptive Optics Production Technology:
    Mask-free direct writing
    Laser ablation and production Medical Technology:
    Laser scanning tomography
    Laser surgery
    Endoscopic head-up displays

| Technical parameters | |
|---|---|
| Pixel size | 16 × 16 µm² |
| Pixel number | 256 × 256 . . . 1024 × 2048 |
| Pixel design | customer-specific, pyramidal, descending, torsion elements, |
| Profile | etc., pyramidal, rectangular, sawtooth, etc. |
| Modulation | phase-modulating or -shifting, deflecting |
| Operation | binary or 4-bit analog |
| Deformation amplitude | 0 . . . 1.2 µm (analog) up to 5.0 µm (binary) |
| Control graph | nonlinear |
| Adjustment time | 10 µs (typ.) |
| Image frequency | 100 Hz . . . 1 kHz |
| Optical filling | 80 . . . 90% |
| Reflectivity | >90% (IR . . . DUV) far UV |

User Evaluation Kit
    In order to provide the possibility of testing all fundamental SLM functions in a user-specific environment, a user evaluation kit containing all components for user-specific image programming of the SLMs was developed.

SLM

| | |
|---|---|
| Pixel size | 16 × 16, 20 × 20, 24 × 24 μm² |
| Pixel number | 256 (160) × 256 |
| Pixel design | customer-specific |
| Operation | 4-bit analog |

SLM Board

| | |
|---|---|
| RAM | Storage of 4 images |
| Image frequency | 1 Hz (PC to PAM) |
| | 500 Hz (RAM to SLM) |
| I/O signals | Matrix Trigger, Matrix Ready |

Data Transfer
  via cable connection and digital I/O interface card for ISA slot on the PC Software
  Conversion of user image data from bitmap into SLM data format
  Control functions for data transfer
  Setting the control voltage level for 4-bit grayscale Requirements
  Windows-compatible PC
  Image pattern generation in bitmap data format, for example using Paintbrush

The invention claimed is:

1. A method of biochip manufacture, which comprises
   (a) providing a programmable illumination matrix and a light sensor detection matrix, wherein said illumination matrix and said detection matrix are arranged facing each other such that the detection matrix is situated in the light path of the illumination matrix and such that the detection matrix can detect light from the illumination matrix;
   (b) positioning a transparent biochip carrier, wherein said carrier has a surface that comprises photoactivatable cleavable protective groups located thereon for photochemical synthesis at predetermined areas of said biochip carrier surface, between said illumination matrix and said detection matrix and in the light path of said illumination matrix such that light from the illumination matrix illuminates and is transmitted through said biochip carrier and to said detection matrix;
   (c) specifically illuminating said biochip carrier to produce an adjustable two-dimensional light exposure pattern that illuminates selected predetermined areas of said biochip carrier;
   (d) monitoring and controlling the quality of said specific two-dimensional light exposure pattern by detecting the location of the illuminated areas of said two-dimensional light exposure pattern on said biochip carrier using the detection matrix and adjusting said two-dimensional light exposure pattern where appropriate, taking into account the information obtained by said monitoring.

2. The method of claim 1, wherein said illumination is electromagnetic radiation selected from the group consisting of infrared, visible, ultraviolet and X-ray radiation.

3. The method of claim 1, wherein said illumination is radiation selected from the group consisting of pulsating radiation, coherent radiation, monochromatic radiation, parallel radiation and radiation which can be focused in different planes.

4. The method of claim 1, wherein said selected predetermined areas are illuminated in parallel.

5. The method of claim 1, wherein said illumination matrix is a reflection matrix having a controllably deformable mirror arrangement.

6. The method of claim 5, wherein said reflection matrix is selected from the group consisting of a light modulator with viscoelastic control layers and a light modulator with micromechanical mirror arrays.

7. The method of claim 1, wherein said illumination matrix is selected from the group consisting of a laser array and a diode array.

8. The method of claim 1, wherein said biochip carrier is an optically transparent carrier.

9. The method of claim 1, wherein said biochip carrier has a surface selected from the group consisting of glass and plastics.

10. The method of claim 1, wherein said selected predetermined areas each are from 1 μm² to 1 cm².

11. The method of claim 1, wherein said selected predetermined areas each are surrounded by nonactivated areas.

12. The method of claim 1, wherein said illumination takes place at a rate of from 1/10000 to 1000 light patterns per second.

13. The method of claim 1, wherein said biochip carrier is precalibrated using the illumination matrix and light sensor detection matrix.

14. The method of claim 1,
   (a) wherein said biochip carrier has a surface which comprises the photoactivatable cleavable protective groups located at predetermined areas of said biochip carrier surface and wherein said programmable illumination matrix is a UV light source array comprising a plurality of individually controllable light sources; and
   (b) wherein said specific two-dimensional light exposure pattern activates said photoactivatable cleavable protective groups at said selected predetermined area areas of said biochip carrier surface.

15. The method of claim 14, which further comprises binding materials selected from the group consisting of (1) biologically functional materials, (2) chemically functional materials, (3) building blocks for said biologically functional materials and (4) building blocks for said chemically functional materials to said activated groups on said selected predetermined areas of said biochip carrier surface.

16. The method of claim 15, wherein said biologically or chemically functional materials or building blocks thereof are selected from the group consisting of nucleic acids, nucleotides, oligonucleotides, nucleic acid analogs, PNA, peptides, proteins, amino acids, saccharides, cells, cell organelles, cell membrane preparations, viral particles, cell aggregates, allergens, pathogens, pharmacological active substances and diagnostic reagents.

17. The method of claim 15, which further comprises synthesizing said biologically or chemically functional materials on said biochip carrier in two or more stages from monomeric or oligomeric building blocks.

18. The method of claim 15, wherein said biologically or chemically functional materials are a library comprising a multiplicity of different biologically or chemically functional materials.

19. The method of claim 14, wherein said activating photoactivatable cleavable protective groups comprises cleaving a protective group at said selected predetermined areas of said biochip carrier surface.

20. The method of claim 15, which further comprises removing materials bound on the carrier.

21. The method of claim 20, wherein said removed materials are used as building blocks for further synthesis of polymers.

22. The method of claim 1, wherein said light sensor detection matrix is a CCD matrix.

23. The method of claim 1, wherein said biochip carrier has a surface selected from the group consisting of silicon, germanium arsenide and gallium arsenide.

24. The method of claim 9, wherein said glass is quartz glass.

25. The method of claim 10, wherein said selected predetermined areas each are from 100 $\mu m^2$ to 1 $mm^2$.

26. The method of claim 12, wherein said illumination takes place at a rate of from 1/10 to 100 light patterns per second.

27. A method of claim 14 wherein said UV light source array is selected from the group consisting of a diode array, a UV laser array, and both a diode array and a UV laser array.

* * * * *